US008530677B2

(12) United States Patent
Coates et al.

(10) Patent No.: US 8,530,677 B2
(45) Date of Patent: Sep. 10, 2013

(54) SUBSTITUTED 3-HYDROXY-DELTA-LACTONES FROM EPOXIDES

(75) Inventors: Geoffrey W. Coates, Lansing, NY (US); John W. Kramer, Mt. Pleasant, MI (US)

(73) Assignee: Cornell University, Ithaca, NY (US)

( * ) Notice: Subject to any disclaimer, the term of this patent is extended or adjusted under 35 U.S.C. 154(b) by 205 days.

(21) Appl. No.: 12/592,280

(22) Filed: Nov. 20, 2009

(65) Prior Publication Data
US 2010/0145046 A1    Jun. 10, 2010

Related U.S. Application Data

(60) Provisional application No. 61/116,609, filed on Nov. 20, 2008.

(51) Int. Cl.
*C07D 309/30*       (2006.01)
*C07D 303/00*       (2006.01)

(52) U.S. Cl.
USPC .......................................... 549/292; 549/512

(58) Field of Classification Search
USPC ................................................ 549/282, 512
See application file for complete search history.

(56) References Cited

PUBLICATIONS

Church et al. Journal of American Chemical Society, 128, 101125-10122, 2006.*
Kramer et al. Organic Letters, 9(26), 5581-5583, 2007.*
Church et al. Journal of American Chemical Society, 126 (31), 10125-10133, 2004.*
Lightburn et al., Organic Letters, 2011, 13(10), 2686-2689.*
Wiese et al., "Hydroformylation," Top. Organomet. Chem. 2006, 18, 1-33.
Aggarwal et al., Application of Sulfur Ylide Mediated Epoxidations in the Asymmetric Synthesis of β-hydroxy-δ-lactones. Synthesis of a Mevinic Acid Analogue and (+)-prelactone B, Tetrahedron, 60, 9726-9733 (2004).
Aprile, C. et al., Studies on the Stereoselective Selenolactonization, Hydroxy and Methoxy Selenenylation of α- and β-Hydroxy Acids and Esters. Synthesis of δ- and γ-Lactones, Tetrahedron, 59, 2241-2251 (2003).
Banerjee, B.; Roy, S. C., Stereoselective Synthesis of Polysubstituted Tetrahydropyrans by Radical Cyclization of Epoxides Using a Transition-Metal Radical Source, Eur. J. Org. Chem., 489-497 (2006).
Bats, J.-P.; Moulines, J.; Leclercq, D., Transposition desoxirannes-ethanols par l'intermediaire d'alcoxyetains, Tetrahedron, 38, 2139-2146 (1982).
Brown, H. C.; Lynch, G. J., Solvomercuration-Demercuration .9. Oxymercuration-Demercuration of Chloromethyl, Epoxymethyl, and Thiomethyl-Substituted Alkenes, J. Org. Chem., 46, 930-939 (1981).
Byrne, C. M. et al., Catalytic Synthesis of Beta3-Amino Acid Derivatives from Alpha-Amino Acids, *Ange. Chemie. Int. Ed.*, 47(21), 3979-3983 (2008).

Cefalo et al., Enantioselective Synthesis of Unsaturated Cyclic Tertiary Ethers by Mo-Catalyzed Olefin Metathesis, J. Am. Chem. Soc., 123, 3139-3140 (2001).
de Lorenzo et al., Statin Therapy-Evidence Beyond Lipid Lowering Contributing to a Plaque Stability, Curr. Med. Chem., 13, 3385-3393 (2006).
Fournier et al., The β-Lactone Route to β-Hydroxy or α,β-Unsaturated Y- and δ-Lactones. Syntheses of (±)-Massoialactone and (±)-Prelactone B, Synlett, 107-111 (2003).
Getzler, Y. D. Y. L et al., Catalytic Carbonylation of β-Lactones to Succinic Anhydrides, J. Am. Chem. Soc., 126, 6842-6843 (2004).
Getzler, Y. D. Y. L. et al., Synthesis of β-Lactones: A Highly Active and Selective Catalyst for Epoxide Carbonylation, J. Am. Chem. Soc., 124, 1174-1175 (2002).
Gijsen et al., Sequential Three- and Four-Substrate Aldol Reactions Catalyzed by Aldolases, J. Am. Chem. Soc., 117, 7585-7591 (1995).
Gogoi, S. et al., First Total Synthesis of Verbalactone, a Macrocyclic Dilactone Isolated from *Verbascum undulatum*, Tetrahedron Lett., 45, 5577-5579 (2004).
Greenberg, W. A. et al., Development of an Efficient, Scalable, Aldolase-Catalyzed Process for Enantioselective Synthesis of Statin Intermediates, Proc. Natl. Acad. Sci. U.S.A., 101, 5788-5793 (2004).
Harrod, J. F.; Chalk, A. J., Dicobalt Octacarbonyl as a Catalyst for Hydrosilation of Olefins, J. Am. Chem. Soc., 87, 1133-1135 (1965).
Heine et al., Analysis of the Class I Aldolase Binding Site Architecture Based on the Crystal Structure of 2-Deoxyribose-5-Phosphate Aldolase at 0.99A Resolution, J. Mol. Biol., 343, 1019-1034 (2004).
Ishikawa, M. et al., Synthesis of the Racemate and Both Enantiomers of Massoilactone, Biosci. Biotechnol. Biochem., 67, 2210-2214 (2003).
Kim et al., Synthesis of Triketide δ-Lactones, Synthesis, 1790-1793 (2001).
Kramer, J. W et al., Practical β-Lactone Synthesis: Epoxide Carbonylation at 1 atm, Org. Lett., 8, 3709-3712 (2006).
Le Sann et al., Assembly Intermediates in Polyketide Biosynthesis: Enantioselective Syntheses of Beta-Hydroxycarbonyl Compounds, Org Biomol. Chem., 3, 1719-1728 (2005).
Loubinoux et al., The Enantioselective Synthesis of Simplified Souther-Half Fragments of Soraphen A, Tetrahedron, 51, 3549-3558 (1995).
MacKeith, R. A. et al., Enzyme-Catalysed Kinetic Resolution of 4-*endo*-Hydroxy-2-Oxabicyclo[3.3.0]oct-7-en-3-one and Employment of the Pure Enantiomers for the Synthesis of Anti-viral and Hypocholestemic Agents, Bioorg. Med. Chem., 2, 387-394 (1994).
Mahadevan, V. et al., [Lewis Acid]+[Co(CO)4]-Complexes: A Versatile Class of Catalysts for Carbonylative Ring Expansion of Epoxides and Aziridines, Angew. Chem. Int. Ed., 41, 2781-2784 (2002).
Molander, G. A. et al., Investigations on 1,2-, 1,3-, and 1,4-Asymmetric Induction in Intramolecular Reformatsky Reactions Promoted by Samarium(II) Iodide, J. Am. Chem. Soc., 113, 8036-8045 (1991).
Murray, R. W. and Gu, H., Dimethyldioxirane Reactions: Rate Acceleration Due to Intramolecular H-Bonding, J. Phys. Org. Chem., 9, 751-758 (1996).

(Continued)

*Primary Examiner* — Nizal Chandrakumar
(74) *Attorney, Agent, or Firm* — Choate, Hall & Stewart LLP; Charles E. Lyon; Danielle M. Nihan

(57) ABSTRACT

Catalysts and methods for the carbonylation of epoxides to substituted 3-hydroxy-δ-lactones and β-lactones are disclosed.

59 Claims, 4 Drawing Sheets

(56) References Cited

PUBLICATIONS

Palombi, L. et al., Diastereoselective Epoxidation of Allylic Alcohols by t-Butyl Hydroperoxide/Zeolites System, Tetrahedron, 53, 11369-11376 (1997).

Reddy et al., Asymmetric Allylboration for the Synthesis of β-Hydroxy-δ-lactone Unit of Statin Drug Analogs, J. Organomet. Chem., 624, 239-243 (2001).

Romeyke, Y. et al., Secondary Metabolites by Chemical Screening-13. Enantioselective Synthesis of δ-Lactones From Streptenol A, A Chiral Building Block From Streptomyces, *Tetrahedron*, 47, 3335-3339 (1991).

Rowley, J. M. et al., Catalytic Double Carbonylation of Epoxides to Succinic Anhydrides: Catalyst Discovery, Reaction Scope, and Mechanism, J. Am. Chem. Soc., 129, 4948-4960 (2007).

Schaus, S. E. et al., Highly Selective Hydrolytic Kinetic Resolution of Terminal Epoxides Catalyzed by Chiral (salen)Co$^{III}$ Complexes. Practical Synthesis of Enantioenriched Terminal Epoxides and 1,2-Diols, J. Am. Chem. Soc., 124, 1307-1315 (2002).

Schmidt, J. A. R. et al., A Readily Synthesized and Highly Active Epoxide Carbonylation Catalyst Based on a Chromium Porphyrin Framework: Expanding the Range of Available β-Lactones, Org. Lett., 6, 373-376 (2004).

Sharma et al., Enzymatic Lactonization Stategy for Enantioselective Synthesis of a Tetrahydrolipstatin Synthon, J. Org. Chem., 64, 8059-8062 (1999).

Stevenson, R. and Weber, J. V., Synthesis of (±)-Parasorbic Acid and (±)-Massoilactone from Meldrum's Acid, J. Nat. Prod., 51, 1215-1219 (1988).

Tobert et al., Lovastatin and Beyond: The History of the HMG-CoA Reductase Inhibitors, Nat. Rev. Drug. Discovery, 2, 517-526 (2003).

\* cited by examiner

SUBSTITUTED 3-HYDROXY-DELTA-LACTONES FROM EPOXIDES

CROSS-REFERENCE TO RELATED APPLICATIONS

This application claims priority to U.S. provisional application Ser. No. 61/116,609, filed Nov. 20, 2008, the entirety of which is hereby incorporated herein by reference.

GOVERNMENT SUPPORT

This work was supported by the National Science Foundation (CHE-0243605) and the Department of Energy (DE-FG02-05ER15687) and by the National Institutes of Health through a Chemical/Biology Interface (CBI) Training Grant.

BACKGROUND

Substituted 3-hydroxy-δ-lactones (3HLs) are common structural motifs in natural products (Aggarwal et al., *Tetrahedron* 2004, 60, 9726-9733) and are valuable as intermediates in the synthesis of a variety of pharmaceutical compounds (Aggarwal et al., *Tetrahedron* 2004, 60, 9726-9733; Sharma et al., *J. Org. Chem.* 1999, 64, 8059-8062; Cefalo et al., *J. Am. Chem. Soc.* 2001, 123, 3139-3140; Stevenson, R.; Weber, J. V. *J. Nat. Prod.* 1988, 51, 1215-1219). 3HLs are most prominent in the class of HMG-CoA reductase inhibitors known as statins, which are among the most potent cholesterol-lowering drugs available and constitute five of the top 100 selling drugs (Tolbert et al., *Nat. Rev. Drug. Discovery*, 2003, 2, 517-526; de Lorenzo et al., *Curr. Med. Chem.* 2006, 13, 3385-3393). All approved statins have side chains comprised of either a 3HL or the hydrolyzed 3,5-dihydroxycarboxylic acid analog (FIG. 1), which are essential for the bioactivity of statin drugs (Aggarwal et al., *Tetrahedron* 2004, 60, 9726-9733). 3HLs have also been used in the synthesis of important drugs such as tetrahydrolipstatin (Sharma et al., *J. Org. Chem.* 1999, 64, 8059-8062), a lipase inhibitor prescribed for the treatment of obesity, and the antiretroviral agent tipranavir (Cefalo et al., *J. Am. Chem. Soc.* 2001, 123, 3139-3140). Furthermore, dehydration of 3HLs produces a class of biologically active α,β-unsaturated lactone natural products (Stevenson, R.; Weber, J. V. *J. Nat. Prod.* 1988, 51, 1215-1219).

As a result of their synthetic value, the synthesis of 3HLs has received a great deal of attention in recent years (Gijsen et al., *J. Am. Chem. Soc.* 1995, 117, 7585-7591; Heine et al., *J. Mol. Biol.* 2004, 343, 1019-1034; Loubinoux et al., *Tetrahedron* 1995, 51, 3549-3558; Kim et al., *Synthesis* 2001, 1790-1793; Le Sann et al., *Org. Biomol. Chem.* 2005, 3, 1719-1728; Reddy et al., *J. Organomet. Chem.* 2001, 624, 239-243; Fournier et al., *Synlett* 2003, 107-111). Biocatalytic routes have proven successful in the synthesis of statin side chains, though substrate scope is limited (Gijsen et al., *J. Am. Chem. Soc.* 1995, 117, 7585-7591; Heine et al., *J. Mol. Biol.* 2004, 343, 1019-1034). Synthetic routes to substituted 3HLs have employed a variety of methods, including aldol reactions using chiral auxiliaries, reduction of diketoesters followed by cyclization, allyl boration and ring-closing metathesis, and rearrangement of β-lactones (Fournier et al., *Synlett* 2003, 107-111). These methods, however, involve multiple steps and can suffer from low stereoselectivity. Thus, there remains a need for improved methodologies to synthesize substituted 3-hydroxy-δ-lactones (3HLs). The present invention provides such a methodology.

SUMMARY

In one aspect the present disclosure provides methods for synthesizing substituted 3-hydroxy-δ-lactones by carbonylation of epoxides. In particular, it has been unexpectedly found that, under certain conditions, the carbonylation of epoxides proceeds to afford predominantly δ-lactones, rather than the expected β-lactone.

In general these methods comprise the steps of:
reacting an epoxide of formula:

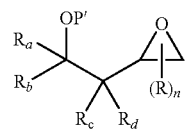

I wherein $R_a$, $R_b$, $R_c$, $R_d$, R, P', and n are as defined below; with carbon monoxide (CO) in the presence of a catalytically effective amount of a catalyst of the formula:

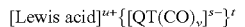

$$[\text{Lewis acid}]^{u+}\{[QT(CO)_v]^{s-}\}^t \quad \text{II}$$

wherein Q, T, s, t, u, and v are as defined below;
to produce a compound of the formula:

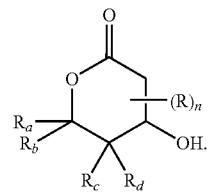

III

In another aspect the present disclosure provides methods for synthesizing β-lactones by carbonylation of epoxides.

All publications and patent documents cited in this application are incorporated by reference in their entirety for all purposes to the same extent as if the contents of each individual publication or patent document were incorporated herein.

DETAILED DESCRIPTION OF CERTAIN EMBODIMENTS

Figure 1:
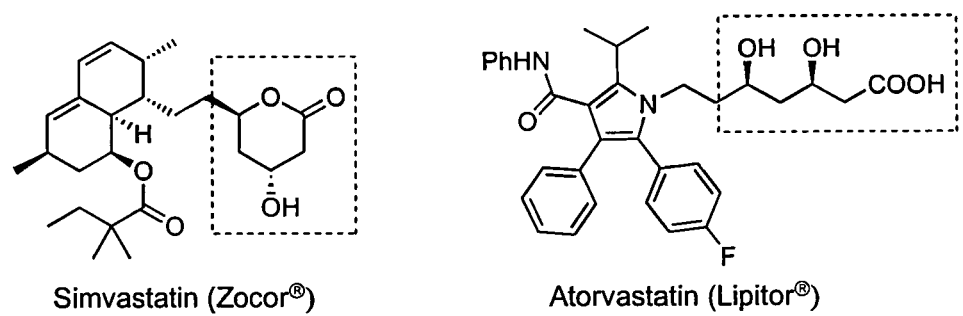
FIG. 1. Structures of two common statin drugs with 3HL portion highlighted.
Figure 2:
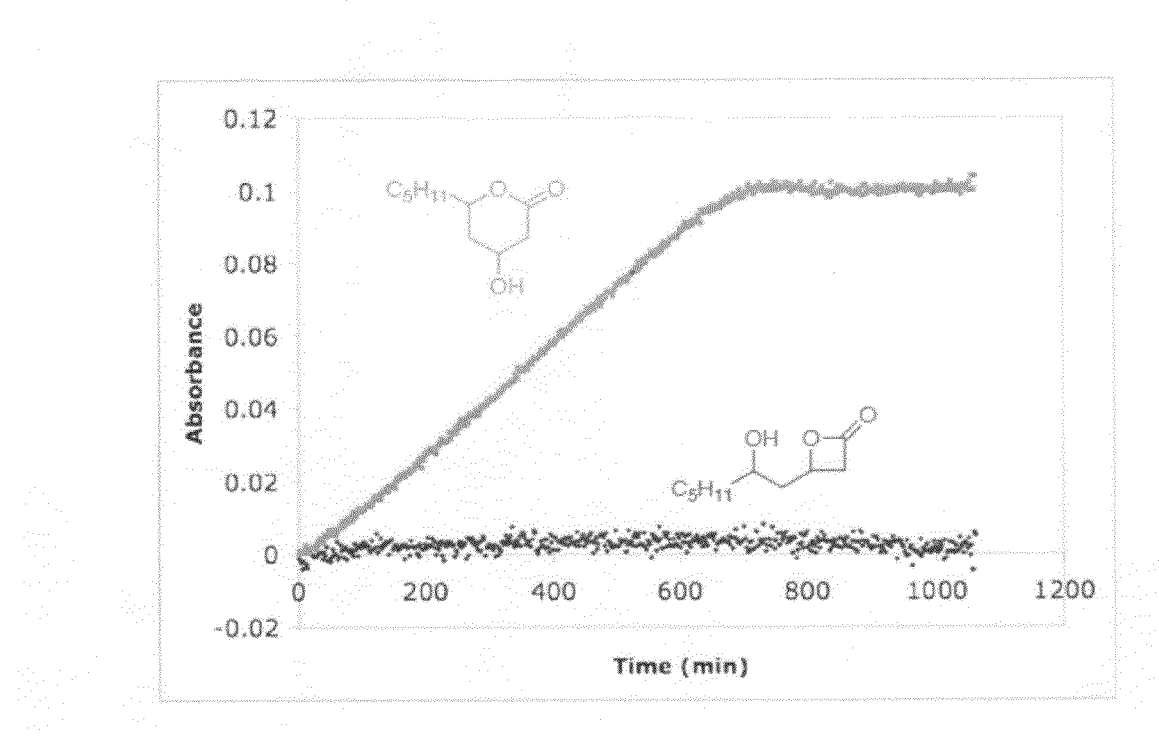
FIG. 2. Carbonylation of 4-hydroxy-1,2-epoxynonane (6) monitored by in situ IR spectroscopy.
Figure 3:
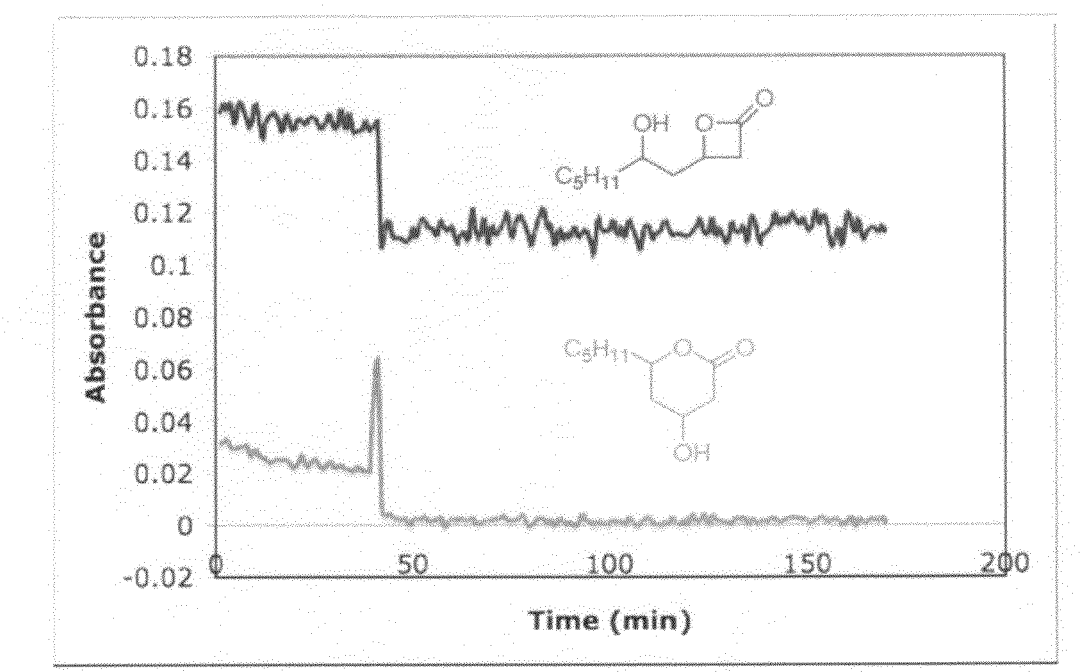
FIG. 3. β-Lactone 8 and δ-lactone 7 under standard reaction conditions monitored by in situ IR spectroscopy. The spike and subsequent drop in absorbances at 40 minutes is due to venting the CO pressure in the reactor and dilution of the reaction mixture by addition of catalyst solution. The unchanging absorbances of both lactones after catalyst addition indicates that 7 is not formed from 8, and therefore 8 is not an intermediate in the carbonylation reaction.
Figure 4:
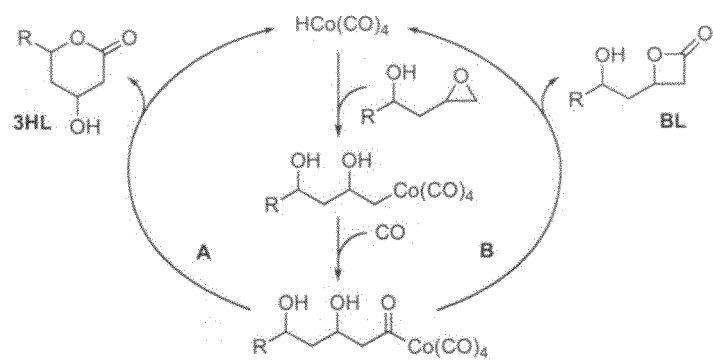
FIG. 4. Proposed Mechanism for Competing δ-Lactone and β-Lactone formation.

The present disclosure provides catalysts and methods that enable the carbonylation of epoxides to provide δ-lactone products and, under certain conditions, β-lactone products. In general, the carbonylation is performed on substituted homoglycidols and proceeds with retention of stereochemistry where stereocenters exist. While methods that produce high crude yields of δ-lactone are most useful (e.g., at least 50%, at least 70%, at least 80%, at least 90%, at least 95%, etc.), the present invention also encompasses methods that generate lower crude yields (e.g., at least 10%, at least 20%, etc.) of δ-lactone, or some amount of β-lactone product. The present disclosure also describes methods that enable the carbonylation of epoxides to provide certain β-lactone products.

In various embodiments, the present disclosure provides a method of producing a δ-lactone, comprising the steps of: reacting an epoxide of formula:

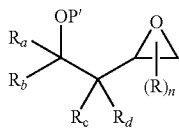

I wherein $R_a$, $R_b$, $R_c$, $R_d$, P', R and n are as defined below; with carbon monoxide (CO) in the presence of a catalytically effective amount of a catalyst of the formula:

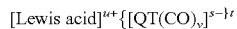

II wherein Q, T, s, t, u, and v are as defined below; to produce a compound of the formula:

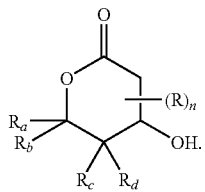

III

Epoxides

The methods are generally applicable and a wide range of epoxide starting materials can be used. The epoxide substrates may be monosubstituted, vicinally disubstituted (either cis or trans), geminally disubstituted, trisubstituted or tetrasubstituted epoxides though these highly substituted substrates react more slowly and tend to give lower yields of product. The substituent(s) on the epoxide can be any that are compatible with the reaction conditions described herein.

In certain embodiments, the epoxide has the formula I:

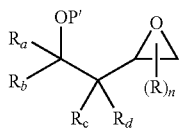

(I)

wherein n is an integer between 0 and 3, inclusive; and the $R_a$, $R_b$, $R_c$, $R_d$, P' and R groups, and any other chemical variable appearing in the Schemes and structures described herein, encompass those chemical moieties and functional groups that would be recognized by one having skill in the art of organic chemistry as being compatible with the structure and function of the molecules bearing those chemical variables. Exemplary functional groups include substituted and unsubstituted, cyclic and acyclic hydrocarbon moieties, substituted and unsubstituted, cyclic and acyclic heteroatom-containing moieties, as well as common functional groups comprising heteroatoms, halogens, and metalloid elements.

To further define the range of suitable groups certain definitions are provided below. Nonetheless, it is to be understood that these definitions are meant to be representative and the absence of a specific group or moiety in the definitions below is not necessarily meant to exclude such groups or to imply that such a group is not encompassed by the present invention.

In any case where a chemical variable is shown attached to a bond that crosses a bond of ring (for example as shown for R above) this means that one or more such variables are optionally attached to the ring having the crossed bond. Each R group on such a ring can be attached at any suitable position, this is generally understood to mean that the group is attached in place of a hydrogen atom on the parent ring. This includes the possibility that two R groups can be attached to the same ring atom. Furthermore, when more than one R group is present on a ring, each may be the same or different than other R groups attached thereto, and each group is defined independently of other groups that may be attached elsewhere on the same molecule, even though they may be represented by the same identifier. Furthermore, when two or more R groups are present, they may be taken together with intervening atoms to form cyclic structures. Such cyclics may optionally contain heteroatoms or sites of unsaturation and may be further substituted with one or more X groups.

In one embodiment of the epoxides of formula I, $R_a$, $R_b$, $R_c$, $R_d$, and each R group can be independently selected from the group consisting of: hydrogen; halogen; (a) $C_1$ to $C_{20}$ alkyl; (b) $C_2$ to $C_{20}$ alkenyl; (c) $C_2$ to $C_{20}$ alkynyl; (d) up to a $C_{12}$ carbocycle; (e) up to a $C_{12}$ heterocycle; (f) —$C(R^{13})_zH_{(3-z)}$; and (g) a polymer chain. Two or more of $R_a$, $R_b$, $R_c$, $R_d$, or R groups may be taken together with the carbon atoms to which they are attached to form one or more rings, and any of (a) through (e) may optionally be further substituted with one or more X groups.

In one embodiment of the epoxides of formula I, P' is hydrogen or a suitable protecting group capable of being cleaved in situ. Suitable protecting groups may be any of those known in the art. In certain embodiments, P' is a protecting group selected from those described in detail in *Protecting Groups in Organic Synthesis*, T. W. Greene and P. G. M. Wuts, 3$^{rd}$ edition, John Wiley & Sons, 1999, the entirety of which is incorporated herein by reference.

X at each occurrence can be independently selected from the group consisting of: halogen; —$OR^{10}$; —$OC(O)R^{13}$; —$OC(O)OR^{13}$; —$OC(O)NR^{11}R^{12}$; —$CN$; —$CNO$; —$C(O)R^{13}$; —$C(O)OR^{13}$; —$C(O)NR^{11}R^{12}$; —$C(R^{13})_zH_{(3-z)}$; —$NR^{11}C(O)R^{10}$; —$NR^{11}C(O)OR^{10}$; —$NCO$; —$NR^{12}SO_2R^{13}$; —$[P(R^{13})_3]^+$; —$P=O(OR^{10})_2$; —$S(O)_xR^{13}$; —$S(O)_2NR^{11}R^{12}$; —$NO_2$; —$N_3$; —$(CH_2)_kR^{14}$; —$(CH_2)_k$—Z—$R^{14}$; and —$(CH_2)_k$—Z—$(CH_2)_m$—$R^{14}$.

$R^{10}$ at each occurrence can be independently selected from the group consisting of: hydrogen; —$C(R^{13})_zH_{(3-z)}$; $C_1$ to $C_{12}$ alkyl; $C_2$ to $C_{12}$ alkenyl; $C_2$ to $C_{12}$ alkynyl; up to a $C_{12}$ carbocycle; up to a $C_{12}$ heterocycle; $S(O)_2R^{13}$; —$Si(R^{15})_3$; and a hydroxyl protecting group.

$R^{11}$ and $R^{12}$ at each occurrence can be independently selected from the group consisting of: hydrogen; $C_1$ to $C_{12}$ alkyl; $C_2$ to $C_{12}$ alkenyl; $C_2$ to $C_{12}$ alkynyl; and —$C(R^{13})_zH_{(3-z)}$. $R^{11}$ and $R^{12}$, when both present, can optionally be taken together with the atom to which they are attached to form a 3- to 10-membered ring.

$R^{13}$ at each occurrence can be independently selected from the group consisting of: hydrogen; halogen; $C_1$ to $C_{12}$ alkyl; $C_2$ to $C_{12}$ alkenyl; $C_2$ to $C_{12}$ alkynyl; up to a $C_{12}$ carbocycle; and up to a $C_{12}$ heterocycle.

$R^{14}$ at each occurrence can be independently selected from the group consisting of: halogen; —$OR^{10}$; —$OC(O)R^{13}$; —$OC(O)OR^{13}$; —$OC(O)NR^{11}R^{12}$; —CN; —CNO; —$C(R^{13})_zH_{(3-z)}$; —$C(O)R^{13}$; —$C(O)OR^{13}$; —$C(O)NR^{11}R^{12}$; —$NR^{11}C(O)R^{13}$; —$NR^{11}C(O)OR^{10}$; —$NR^{11}SO_2R^{13}$; —NCO; —$N_3$; —$NO_2$; —$S(O)_xR^{13}$; —$SO_2NR^{11}R^{12}$; up to a $C_{12}$ heterocycle; and up to a $C_{12}$ carbocycle.

$R^{15}$ at each occurrence can be independently selected from the group consisting of: $C_1$ to $C_6$ alkyl; $C_2$ to $C_6$ alkenyl; $C_2$ to $C_6$ alkynyl; and up to $C_{12}$ substituted or unsubstituted carbocycle.

Z is a divalent linker and can be selected from the group consisting of: —(CH=CH)$_a$—; —(CH≡CH)$_a$—; —C(O)—; —C(=$NOR^{11}$)—; —C(=$NNR^{11}R^{12}$)—; —O—; —N($R^{11}$)—; —N(C(O)$R^{13}$)—; —S(O)$_x$—; a polyether; and a polyamine.

a can be 1, 2, 3, or 4.

k can be an integer from 1 to 8 inclusive.

m can be an integer from 1 to 8 inclusive.

x can be 0, 1, or 2.

z can be 1, 2, or 3.

In certain embodiments, R is an optionally substituted branched aliphatic moiety.

In certain embodiments, the epoxide is of the formula

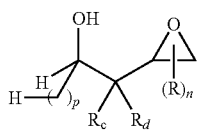

wherein p is an integer between 0 and 10, inclusive. In certain embodiments, $R_c$, $R_d$, and R are hydrogen. In some embodiments, p is 0. In some embodiments, p is 1. In some embodiments, p is 2. In some embodiments, p is 3. In some embodiments, p is 4.

In certain embodiments, the epoxide is of the formula

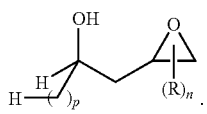

In certain embodiments, the epoxide is of the formula

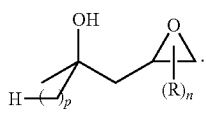

In certain embodiments, the epoxide is of the formula

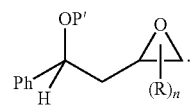

In certain embodiments, the epoxide is of the formula

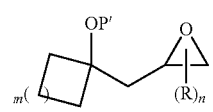

wherein m is an integer between 0 and 10, inclusive. In certain embodiments, m is 2. In certain embodiments, m is 9. In certain embodiments, m is 1, 2, 3, 4, 5, 6, 7, 8, 9, or 10. In certain embodiments, n is 0. In some embodiments, P' is hydrogen.

In some of these embodiments, the epoxide is of the formula

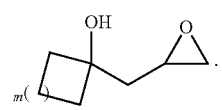

In certain embodiments, the epoxide is of the formula

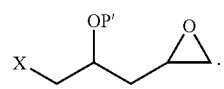

In certain embodiments, X is halogen. In certain embodiments, X is chlorine.

In certain embodiments, X is a phosphorous containing functional group. In certain embodiments, X is a phosphonium salt. In certain embodiments, X is —[P($R^{13}$)$_3$]$^+$. In certain embodiments, X is triarylphosphonium. In certain embodiments, X is triphenylphosphonium. In certain embodiments, X is a phosphonate group. In certain embodiments, X is P=O(O$R^{10}$)$_2$. In certain embodiments, X is P=O(OMe)$_2$. In certain embodiments, X is P=O(OEt)$_2$.

In certain embodiments, X is a keto group =O. In certain embodiments, X is an acetal group.

In certain embodiments the epoxide is of the formula

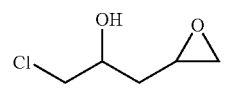

In certain embodiments, the epoxide is of the formula

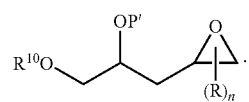

In some embodiments, $R^{10}$ and P' are hydrogen. In some embodiments, $R^{10}$ and P' are suitable protecting groups. In certain embodiments, a suitable protecting group is a silyl protecting group. In some instances, the suitable protecting group is tert-butyldimethylsilyl.

In certain embodiments, the epoxide is of the formula $$R^{10}O\diagdown\diagup\underset{OH}{\diagup}\diagdown\diagup\underset{(R)_n}{\triangle O}.$$

In some embodiments, $R^{10}$ is an aliphatic group optionally substituted with fluorine.

In certain embodiments, the epoxide is of the formula $$TBDMSO\diagdown\diagup\underset{OH}{\diagup}\diagdown\diagup\underset{(R)_n}{\triangle O}.$$

In certain embodiments, the epoxide is of the formula $$TBDMSO\diagdown\diagup\underset{OH}{\diagup}\diagdown\diagup\triangle O.$$

In certain embodiments, the epoxide is of the formula $$HF_2CF_2CO\diagdown\diagup\underset{OH}{\diagup}\diagdown\diagup\triangle O.$$

In certain embodiments, the epoxide is of the formula $$\diagup\diagdown\diagup\underset{OP'}{\diagup}\diagdown\diagup\underset{(R)_n}{\triangle O}.$$

In some embodiments, n is 0. In some embodiments, P' is hydrogen.

In certain embodiments, the epoxide is of the formula $$\diagup\diagdown\diagup\underset{OH}{\diagup}\diagdown\diagup\triangle O.$$

Where different stereoisomers of an epoxide can exist, the epoxide may or may not contain more than one stereoisomer. In certain embodiments, the epoxide may be a single enantiomer or diastereomer. In certain embodiments, the epoxide is of the formula $$\diagdown\diagup\diagdown\diagup\underset{OH}{\diagup}\diagdown\diagup\triangle O.$$

In certain embodiments wherein the epoxide is enantiopure, carbonylation may proceed with retention of stereochemistry.

It is to be understood that the present invention encompasses the use of epoxides which comprise any combination of these variable definitions.

These representative epoxides demonstrate that the methods are applicable to a range of substituted epoxide substrates including those containing alcohols, ethers, silyl ethers, alkenes and halogens. It is to be understood that these lists are not exhaustive and that other functional groups can also be present.

In certain embodiments, the 3-hydroxy-δ-lactones produced according to the disclosed methods are useful as pharmaceutical compounds or as intermediates in the synthesis of pharmaceutical compounds. In certain embodiments, the disclosed methods are useful in the synthesis of cholesterol-lowering agents. In certain embodiments, the present invention provides methods for the synthesis of statin drugs and their derivatives and precursors.

In certain embodiments, the 3-hydroxy-δ-lactones produced by methods of the invention represent a statin sidechain having the formula S-I:

S-I where Q' is as defined herein.

In certain embodiments, the invention encompasses methods comprising the step of carbonylating an epoxide of formula S-Ia with a carbonylation catalyst and CO to provide a compound of formula S-I:

S-Ia → catalyst, CO → S-I

In certain embodiments, the methods further include the step of opening the lactone ring to provide molecules, of structure S-II:

S-I → R—OH → S-II

In certain embodiments, the ring opening step is performed in the presence of water and R in structure S-II is H.

In certain embodiments, the starting epoxide is enantioenriched and the method provides statin-like compounds with defined stereochemistry such as S-I':

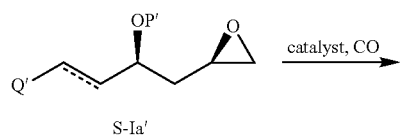

S-Ia'

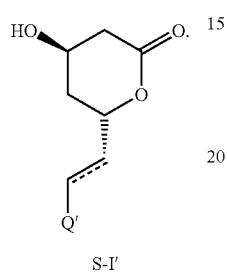

S-I'

In certain embodiments -Q' in the above schemes and structures is selected from the group consisting of: hydrogen; halogen; (a) $C_1$ to $C_{20}$ alkyl; (b) $C_2$ to $C_{20}$ alkenyl; (c) $C_2$ to $C_{20}$ alkynyl; (d) up to a $C_{16}$ carbocycle; (e) up to a $C_{1-6}$ heterocycle; (f) —$C(R^{13})_zH_{(3-z)}$; and (g) a polymer chain.

In certain embodiments Q' in the above schemes and structures is selected from the group consisting of the core of a statin compound or a precursor or derivative of such a compound. In certain embodiments, Q' is the core of a compound selected from the group consisting of: atorvastatin, cerivastatin, fluvastatin, lovastatin, mevastatin, pitavastatin, pravastatin, rosuvastatin, and simvastatin.

In certain embodiments, the invention comprises methods to produce atorvastatin, and precursors and derivatives thereof. In certain embodiments, the moiety

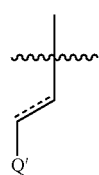

is selected from the group consisting of:

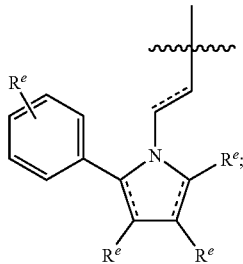 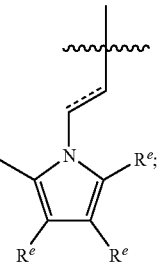

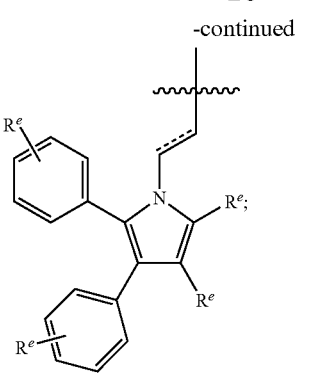

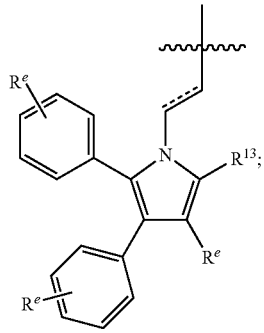

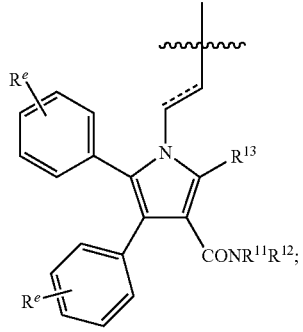

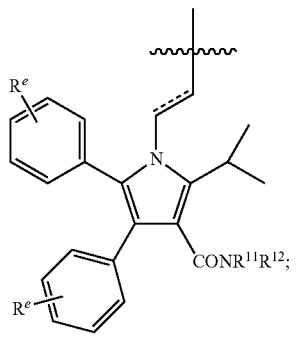

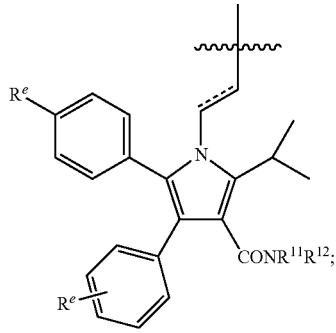

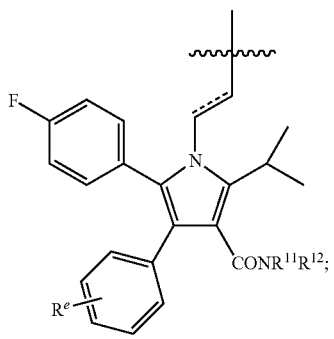
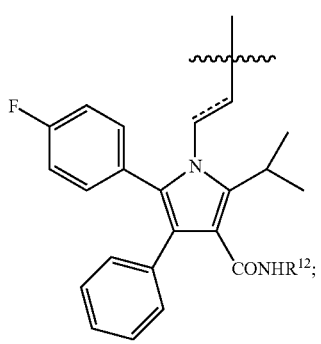
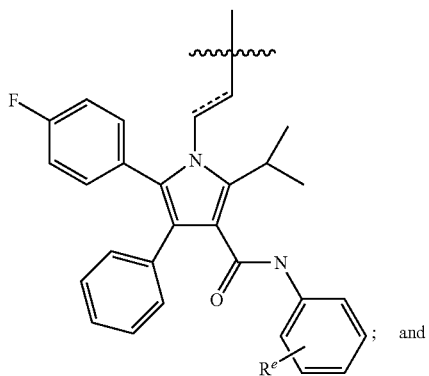
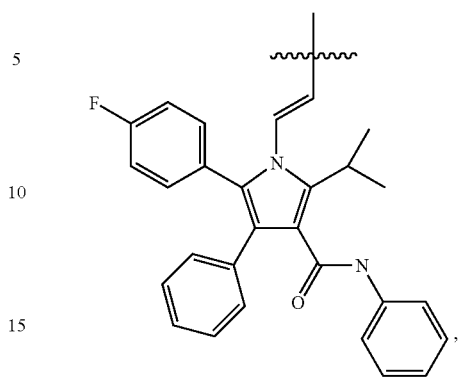
where $R^{11}$, $R^{12}$, and $R^{13}$ are as defined herein above and $R^e$ is as defined below.
In certain embodiments, the invention comprises methods to produce cerivastatin and precursors and derivatives thereof. In certain embodiments, the moiety
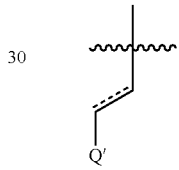
is selected from the group consisting of:
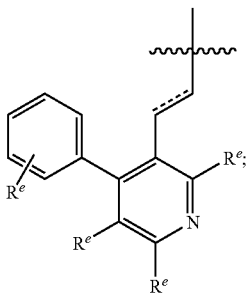
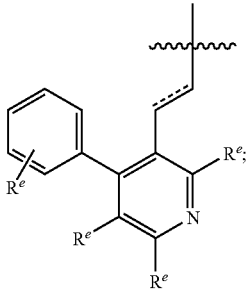

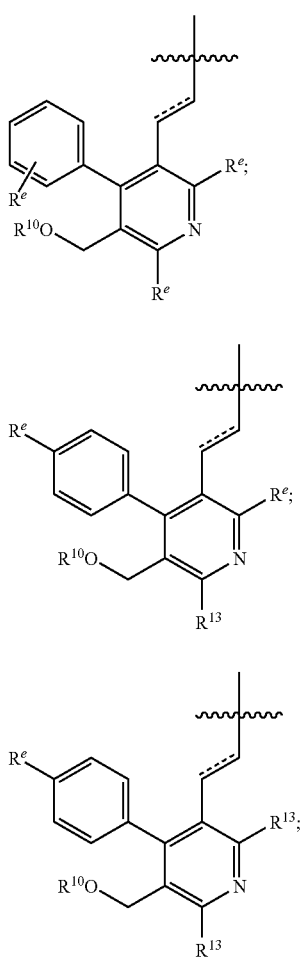
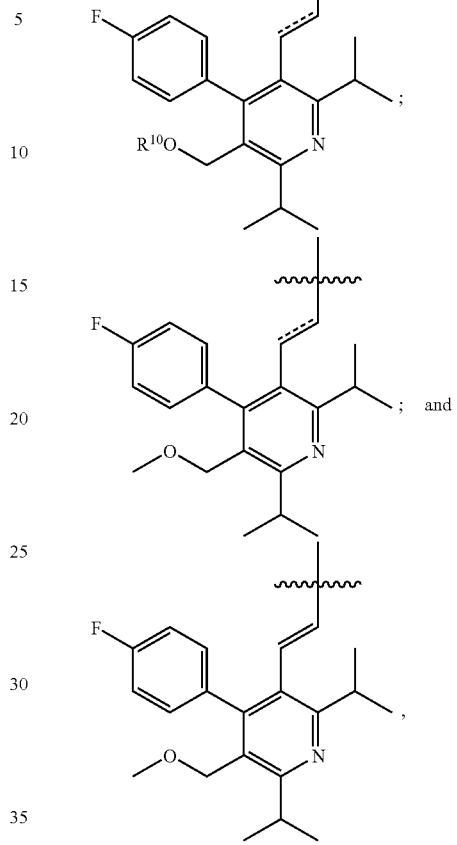
where $R^{10}$ and $R^{13}$ are as defined herein above and $R^e$ is as defined below.
In certain embodiments, the invention comprises methods to produce fluvastatin, and precursors and derivatives thereof. In certain embodiments, the moiety
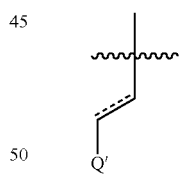
is selected from the group consisting of:
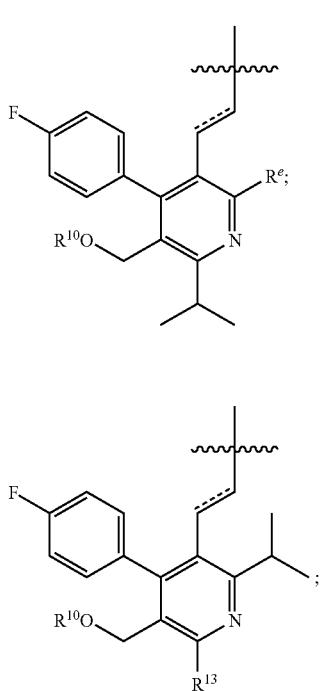
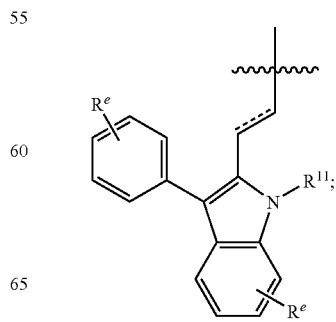

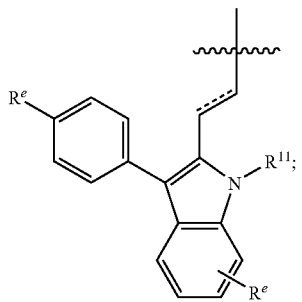
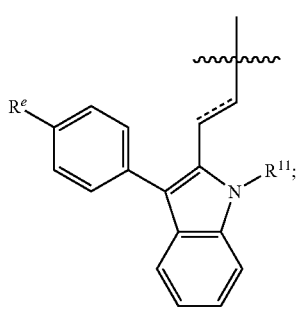
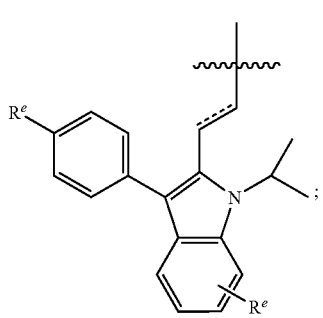
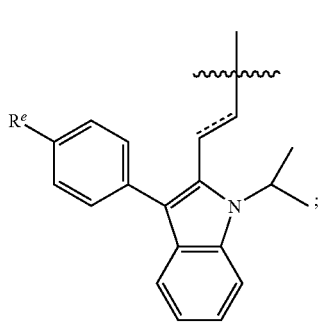
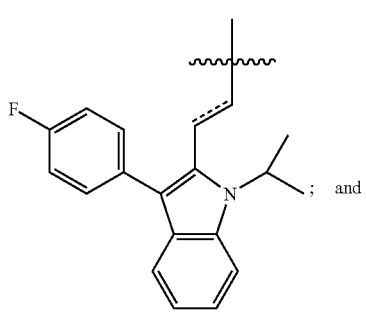
and
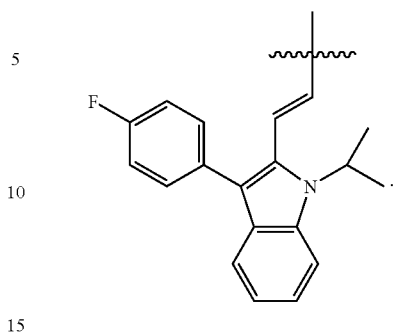
In certain embodiments, the invention comprises methods to produce lovastatin, and precursors and derivatives thereof. In certain embodiments, the moiety
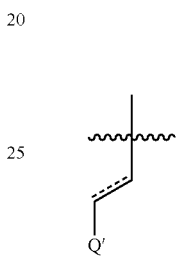
is selected from the group consisting of:
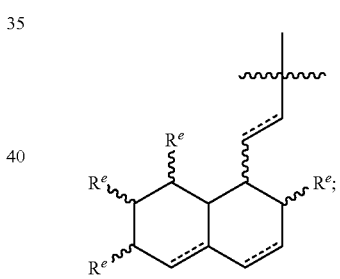
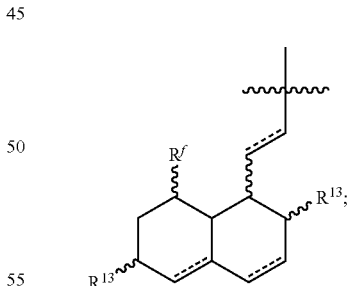
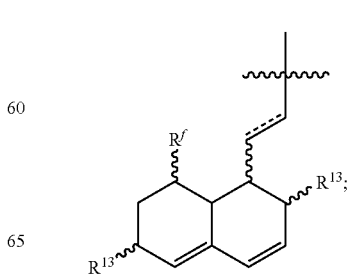

-continued
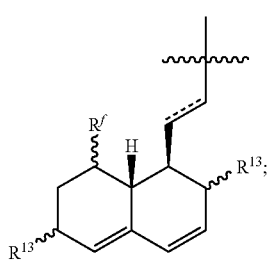
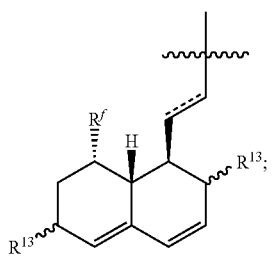
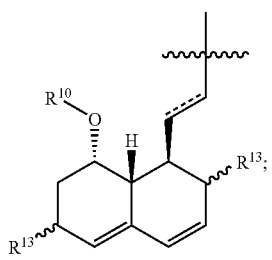
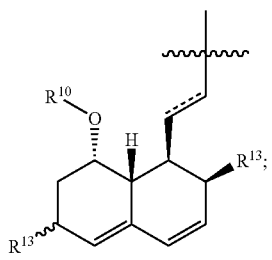
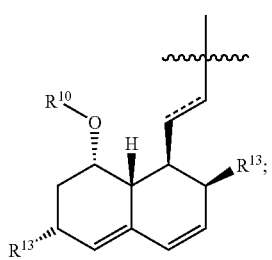
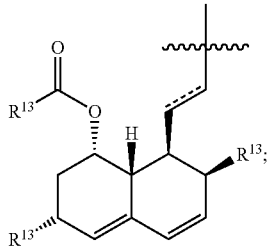
-continued
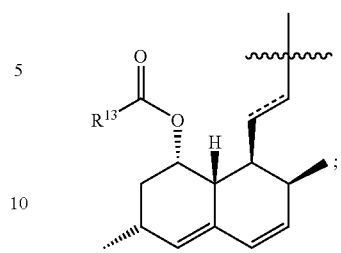
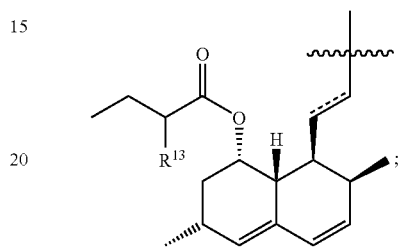
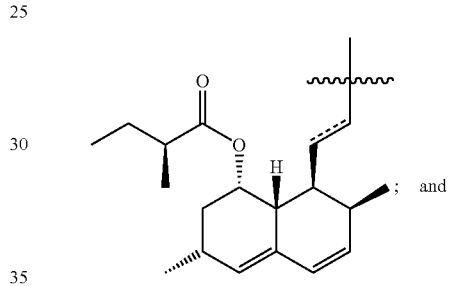
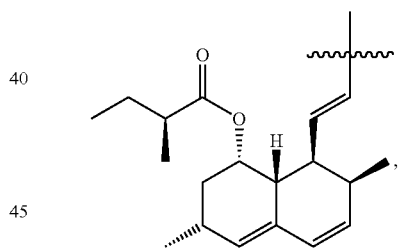
where $R^{10}$ and $R^{13}$ are as defined herein above and $R^e$ and $R^f$ are as defined below.
In certain embodiments, the invention comprises methods to produce simvastatin, and precursors and derivatives thereof. In certain embodiments, the moiety
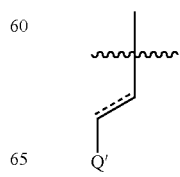

is selected from the group consisting of:

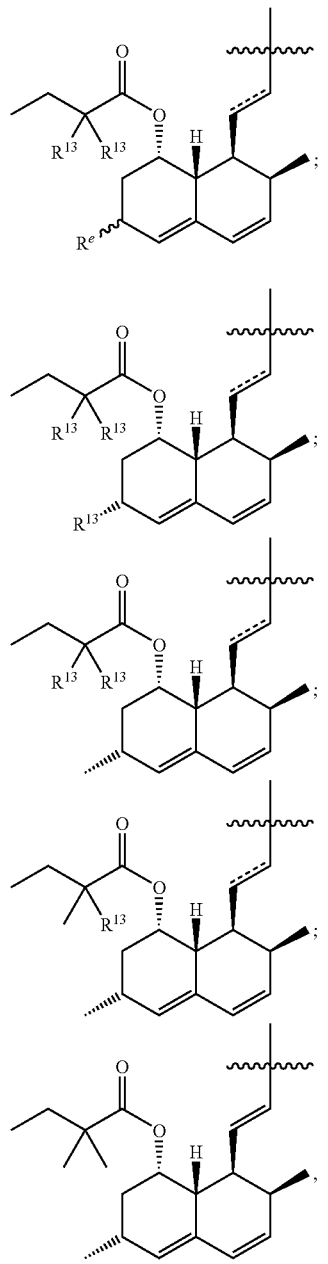

where $R^{13}$ is as defined herein above and $R^e$ is as defined below.

In certain embodiments, the invention comprises methods to produce mevastatin, and precursors and derivatives thereof. In certain embodiments, the moiety

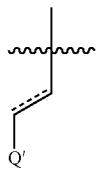

is selected from the group consisting of:

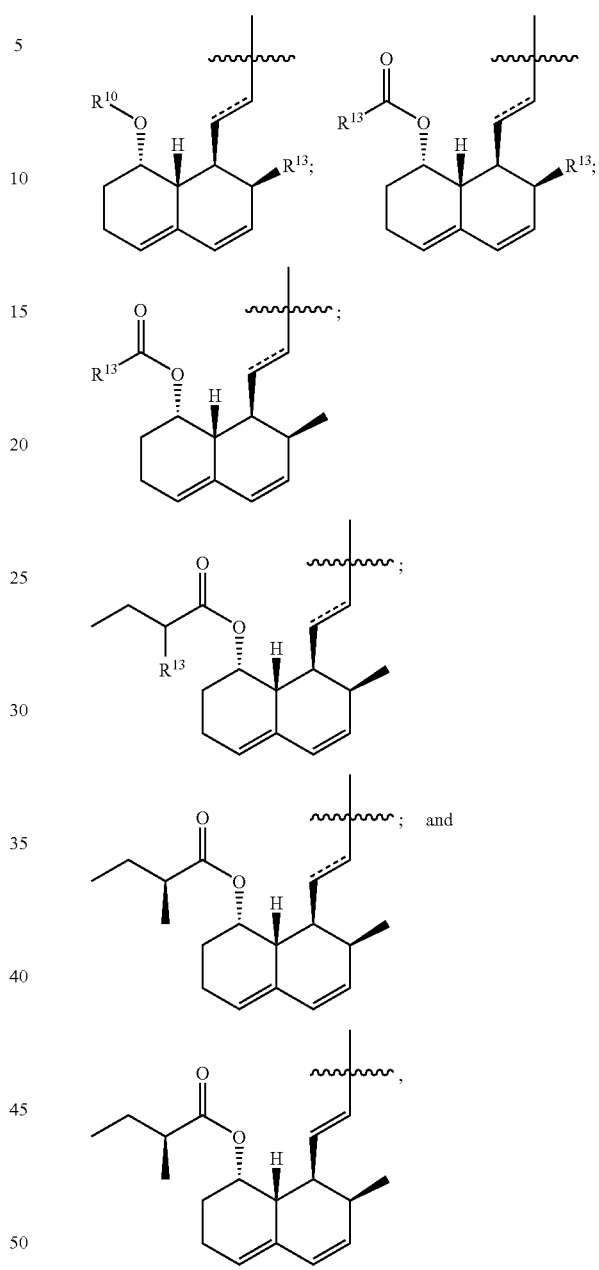

where $R^{10}$ and $R^{13}$ are as defined herein above.

In certain embodiments, the invention comprises methods to produce pravastatin, and precursors and derivatives thereof. In certain embodiments, the moiety

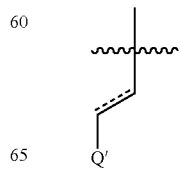

is selected from the group consisting of:
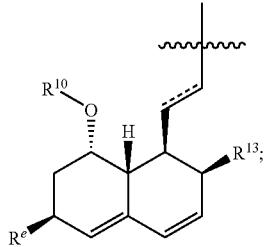
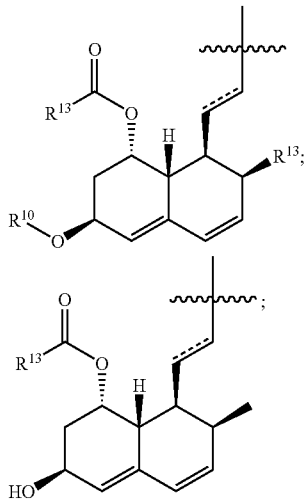
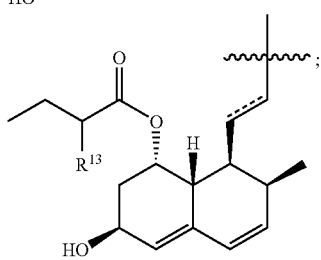
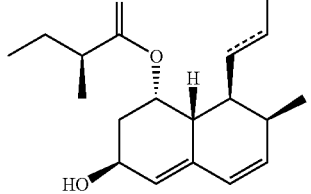
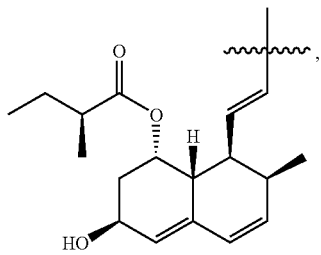
where $R^{10}$ and $R^{13}$ are as defined hereinabove and $R^e$ is as defined below.
In certain embodiments, the invention comprises methods to produce pitavastatin, and precursors and derivatives thereof. In certain embodiments, the moiety
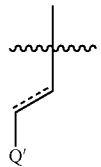
is selected from the group consisting of:
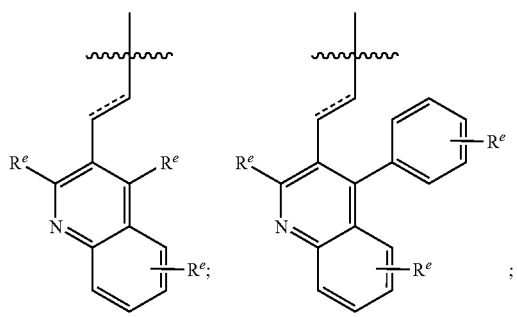
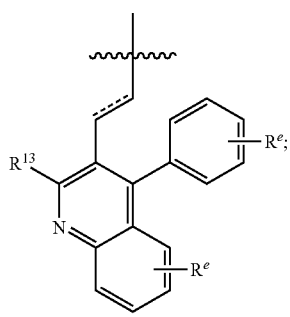
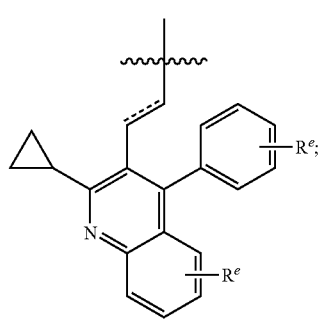
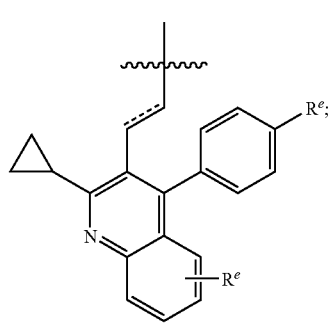

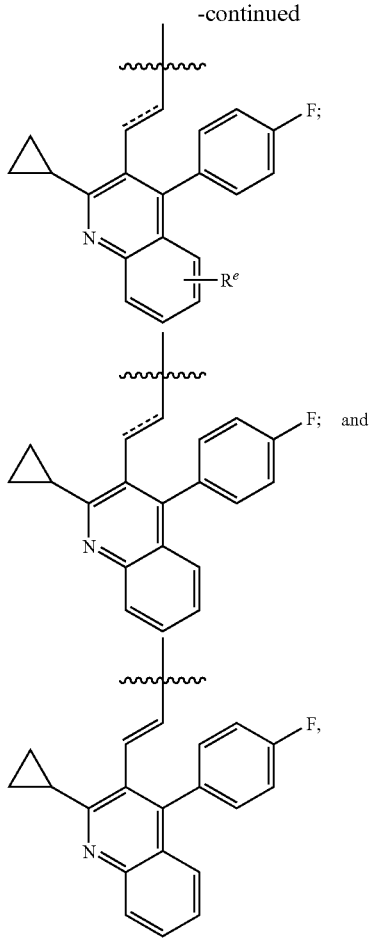
where $R^{13}$ is as defined herein above and $R^e$ is as defined below.
In certain embodiments, the invention comprises methods to produce rosuvastatin, and precursors and derivatives thereof. In certain embodiments, the moiety
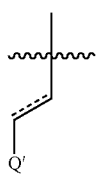
is selected from the group consisting of:
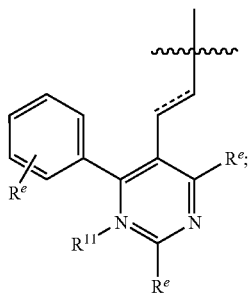
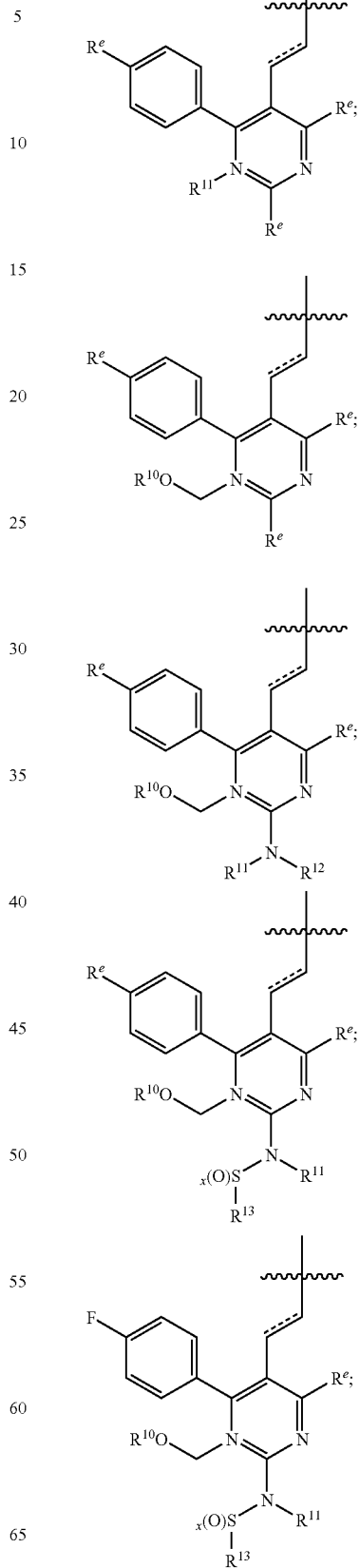

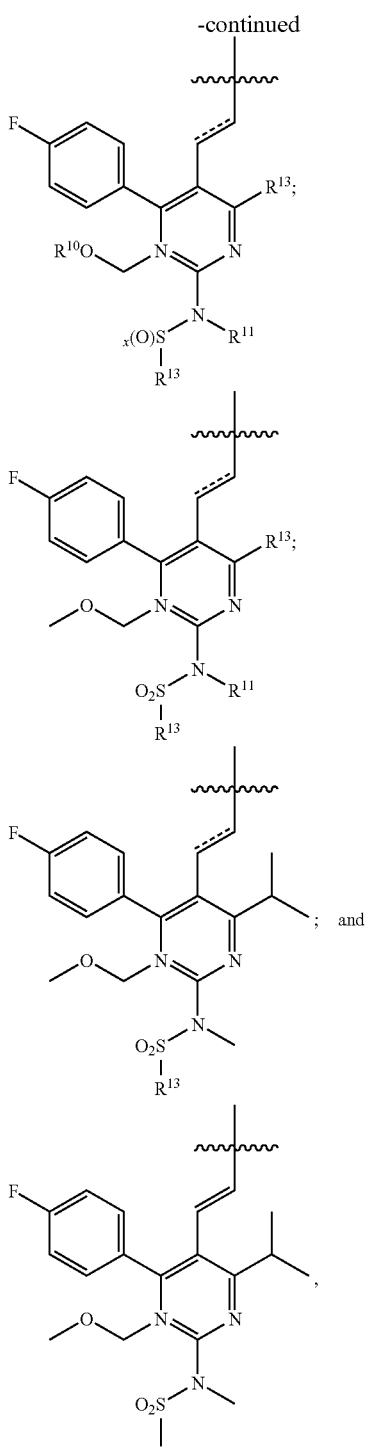

where $R^{10}$ $R^{11}$ $R^{12}$ and $R^{13}$ are as defined herein above and $R^e$ is as defined below.

Catalysts

As described generally above, the present invention encompasses the use of carbonylation catalysts of formula II:

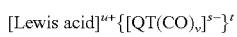

wherein:
Q is any ligand or set of ligands and need not be present;
T is a transition metal;
s is an integer from 1 to 4 inclusive;
t is a number such that t multiplied by s equals u;
u is an integer from 1 to 6 inclusive; and
v is an integer from 1 to 9 inclusive.

In some embodiments, v is an integer from 1 to 4 inclusive. In certain embodiments, v is 4.

In certain embodiments, u and s are both 1. In certain embodiments, u and s are both 2.

Transition Metal Carbonyl Complexes

The transition metal carbonyl complex included in the catalyst may be neutral or anionic. In certain embodiments, the metal carbonyl complex is anionic, e.g., monoanionic carbonyl complexes of metals from groups 5, 7 or 9 of the periodic table or dianionic carbonyl complexes of metals from groups 4 or 8 of the periodic table. In certain embodiments, the metal carbonyl complex contains a metal from group 9 of the periodic table, e.g., cobalt. In certain embodiments [Co(CO)$_4$]$^-$ may be used.

In some embodiments, the transition metal carbonyl complex of a carbonylation catalyst is neutral and no Lewis acid as set forth in formula II is present. In certain embodiments, the carbonylation catalyst is Co$_2$(CO)$_8$.

While the metal carbonyl complexes disclosed herein are generally binary metal carbonyl complexes (i.e., they have the formula T(CO)$_v$ and consist only of a metal and carbonyl ligands) this is not a limiting requirement of the present invention, and the use of mixed ligand metal carbonyl complexes is also contemplated. For example, a bidentate phosphine ligand may be present along with the carbonyl ligands. It is also anticipated that under some reaction conditions, mixed ligand carbonyl complexes may be formed in situ from the binary complexes during the reaction. Whether added or formed in situ, catalysts containing mixed ligand carbonyl complexes are encompassed by the present invention.

In some cases, the metal atom of the Lewis acid can be coordinated to one or more additional neutral coordinating ligands (for instance to satisfy the metal atom's coordination valence) one such ligand that is particularly preferred is tetrahydrofuran (THF), it will be understood however that many other solvents and other ligands such as are well known in the art may also fulfill this role without departing from the present invention. It will also be realized that under reaction conditions, the coordinating ligands can be replaced by reagents, products, intermediates or solvents that may be present. Such in situ-generated species are also encompassed by the present invention. As with many catalytic processes, the structure of the specific catalyst added to the reaction will not always be the active species.

Lewis Acids

In some embodiments, the present invention encompasses the use of carbonylation catalysts comprising a complex of formula [Lewis acid]$^{u+}${[QT(CO)$_v$]$^{s-}$}$^t$, wherein Q, T, s, t, u, and v are as defined above. In some embodiments, the Lewis acid is H$^+$. In certain embodiments, a carbonylation catalyst is of the formula HCo(CO)$_4$. In some embodiments, Lewis acids are metal complexes of the formula [M(L)$_b$]$^{c+}$ (e.g., where M is a metal, each L is a ligand and need not be present, b is an integer from 1 to 6 inclusive, and c is 1, 2, or 3, and where, if more than one L is present, each L may be the same or different). In certain embodiments, M is a transition metal or a group 13 or 14 metal. For example, in some embodiments, M is aluminum, chromium, or titanium. In certain embodiments, M is aluminum.

Similarly, a range of ligands (L) can be present in the Lewis acid of the carbonylation catalyst. In certain embodiments a ligand can be a dianionic tetradentate ligand. In some embodiments, a ligand can be a solvent such as THF. In certain embodiments, Lewis acids of the carbonylation catalyst contain a combination of one or more dianionic tetradentate ligands and one or more solvent ligands (e.g., THF).

Suitable ligands include, but are not limited to, porphyrin derivatives of formula IIIa, salen derivatives of formula IIIb, and metallocene derivatives of formula IIIc, below. In some cases, a mixture of more than one Lewis acid can be present in the catalyst. Exemplary definitions for the R groups appearing in structures IIIa, IIIb, and IIIc are more fully described above and herein.

In certain embodiments, a Lewis acid of a carbonylation catalyst is of formula IIIa:

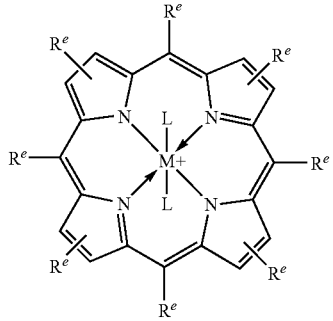

IIIa wherein:
M is a metal;
L is a ligand and need not be present;
$R^e$ at each occurrence is independently selected from the group consisting of: hydrogen; $C_1$-$C_{12}$ alkyl; $C_2$-$C_{12}$ alkenyl; $C_2$-$C_{12}$ alkynyl; aryl; heteroaryl; halogen; —$OR^{10}$; —$OC(O)R^{13}$; —$OC(O)OR^{13}$; —$OC(O)NR^{11}R^{12}$; —CN; —CNO; —$C(O)R^{13}$; —$C(R^{13})_zH_{(3-z)}$; —$C(O)OR^{13}$; —$C(O)NR^{11}R^{12}$; —$NR^{11}R^{12}$; —$NR^{11}C(O)R^{10}$; —$NR^{11}C(O)OR^{13}$; —$NR^{11}SO_2R^{13}$; —NCO; —$N_3$; —$NO_2$; —$S(O)_xR^{13}$; —$SO_2NR^{11}R^{12}$; —$C(R^{13})_zH_{(3-z)}$; —$(CH_{12})_kR^{14}$; —$(CH_2)_k$—Z—$R^{16}$—; and —$(CH_2)_k$—Z—$(CH_2)_m$—$R^{14}$; where two or more Re groups can optionally be taken together with intervening atoms to form an optionally substituted carbocyclic or heterocyclic ring, and
$R^{10}$, $R^{11}$, $R^{12}$, $R^{13}$, $R^{14}$, $R^{16}$, Z, k, m, x, and z are as defined above.

In some embodiments, each occurrence of $R^e$ is independently hydrogen; halogen; $C_1$-$C_{12}$ alkyl; $C_2$-$C_{12}$ alkenyl; $C_2$-$C_{12}$ alkynyl; aryl; or heteroaryl.

In some embodiments, each occurrence of $R^e$ is independently hydrogen, halogen, or $C_1$-$C_6$ alkyl. In certain embodiments, each occurrence of $R^e$ is independently methyl, ethyl, propyl, or butyl. In certain embodiments, $R^e$ is ethyl.

In some embodiments, each occurrence of $R^e$ is independently aryl. In certain embodiments, each occurrence of $R^e$ is independently phenyl optionally substituted with 1-3 substituents selected from the group consisting of fluorine, chlorine, methyl, trifluoromethyl, methoxy, and/or trifluoromethoxy. In certain embodiments, each occurrence of $R^e$ is independently phenyl substituted at the para position with a substituent selected from the group consisting of fluorine, chlorine, methyl, trifluoromethyl, methoxy, or trifluoromethoxy. In certain embodiments, each occurrence of $R^e$ is independently phenyl substituted at the ortho and para positions with methyl.

In some embodiments, a Lewis acid of the carbonylation catalyst is of formula IIIa, wherein M is Al.

In some embodiments, a Lewis acid of the carbonylation catalyst is of formula IIIa, wherein L is a solvent. In certain embodiments, a Lewis acid of the carbonylation catalyst is of formula IIIa and L is an ethereal solvent. In certain embodiments, a Lewis acid of the carbonylation catalyst is of formula IIIa and each L is THF.

In some embodiments, a Lewis acid of the carbonylation catalyst is of formula IIIa(i):

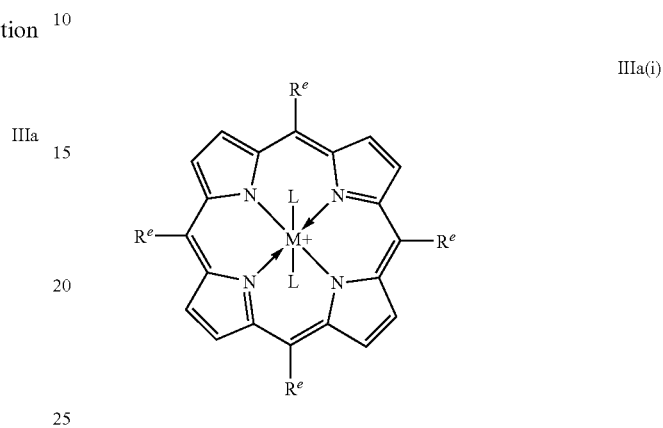

IIIa(i)

wherein L, M, and $R^e$ are as defined above and herein. In some embodiments, a Lewis acid of the carbonylation catalyst is of formula IIIa(i), wherein M is Al or Cr. In some embodiments, a Lewis acid of the carbonylation catalyst is of formula IIIa(i), wherein L is a solvent. In certain embodiments, a Lewis acid of the carbonylation catalyst is of formula IIIa(i) and L is an ethereal solvent. In certain embodiments, a Lewis acid of the carbonylation catalyst is of formula IIIa(i) and each L is THF.

In some embodiments, a Lewis acid of the carbonylation catalyst is of formula IIIa(ii):

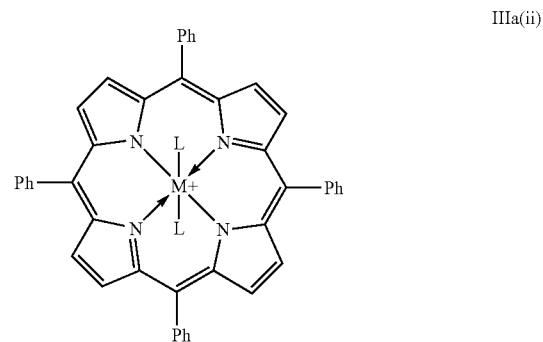

IIIa(ii)

wherein L and M are as defined above and herein.

In some embodiments, a Lewis acid of the carbonylation catalyst is of formula IIIa(ii), wherein L is a solvent. In certain embodiments, a Lewis acid of the carbonylation catalyst is of formula IIIa(ii) and L is an ethereal solvent. In certain embodiments, a Lewis acid of the carbonylation catalyst is of formula IIIa(ii) and each L is THF. In certain embodiments, wherein a Lewis acid of the carbonylation catalyst is of formula IIIa(ii), the transition metal complex is $[Co(CO)_4]^-$. In certain embodiments, wherein a Lewis acid of the carbonylation catalyst is of formula IIIa(ii), M is Al or Cr.

In certain embodiments, a carbonylation catalyst is of formula IIa(i):

IIa(i)

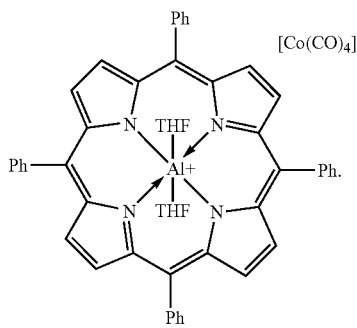

In certain embodiments, a carbonylation catalyst is of formula IIa(ii):

IIa(ii)

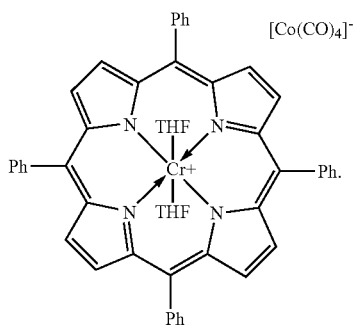

In certain embodiments, a Lewis acid of the carbonylation catalyst is of formula IIIb:

IIIb

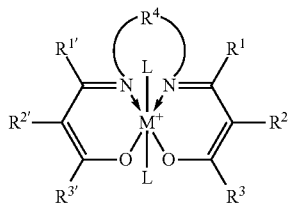

wherein:

$R^1$ and $R^{1'}$ are independently selected from the group consisting of: hydrogen; $C_1$ to $C_{12}$ alkyl; $C_2$ to $C_{12}$ alkenyl; $C_2$ to $C_{12}$ alkynyl; —C$(R^{13})_z$H$_{(3-z)}$; —(CH$_2$)$_k$R$^{14}$; and —(CH$_2$)$_k$—Z—R$^{14}$;

$R^2$, $R^{2'}$, $R^3$, and $R^{3'}$ are independently selected from the group consisting of:

(i) $C_1$-$C_{12}$ alkyl; (ii) $C_2$-$C_{12}$ alkenyl; (iii) $C_2$-$C_{12}$ alkynyl; (iv) up to a $C_{12}$ carbocycle; (v) up to a $C_{12}$ heterocycle; (vi) —(CH$_2$)$_k$R$^{14}$; (vii) R$^{20}$; and (viii) —C(R$^{13}$)$_z$H$_{(3-z)}$, wherein each of (i) through (v) may optionally be further substituted with one or more R$^{20}$ groups; and where $R^2$ and $R^3$, and $R^{2'}$ and $R^{3'}$ may optionally be taken together with the carbon atoms to which they are attached to form one or more rings which may in turn be substituted with one or more R$^{20}$ groups;

$R^4$ is selected from the group consisting of:

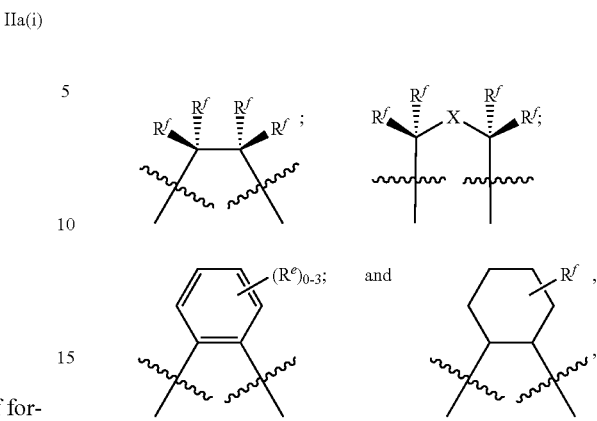

wherein X is a divalent linker selected from the group consisting of: —N(R$^{11}$)—; —S(O)$_x$; —(CH$_2$)$_k$—; —C(O)—; —C(=NOR$^{10}$)—; —C(R$^f$)$_2$—; a polyether; a $C_3$ to $C_8$ substituted or unsubstituted carbocycle; and a $C_1$ to $C_8$ substituted or unsubstituted heterocycle;

$R^e$ is as defined above;

$R^f$ at each occurrence is independently selected from the group consisting of: (a) $C_1$-$C_{12}$ alkyl; (b) $C_2$-$C_{12}$ alkenyl, (c) $C_2$-$C_{12}$ alkynyl; (e) up to a $C_{12}$ carbocycle, (f) up to a $C_{12}$ heterocycle; (g) R$^{20}$; and (h) —C(R$^{13}$)$_z$H$_{(3-z)}$; or wherein:

two or more R$^f$ groups may be taken together with intervening atoms to form one or more rings; or wherein when two R$^f$ groups are attached to the same carbon atom, they may be taken together to form a moiety selected from the group consisting of: a 3- to 8-membered spirocyclic ring; a carbonyl (C=O), an oxime)(C=NOR$^{10}$; a hydrazone (C=NNR$^{11}$R$^{12}$); an imine (C=NR$^{11}$); and an alkenyl group (C=CR$^{11}$R$^{12}$);

$R^{20}$ at each occurrence is independently selected from the group consisting of: hydrogen; halogen; —OR$^{10}$; —OC(O)R$^{13}$; —OC(O)OR$^{13}$; —OC(O)NR$^{11}$R$^{12}$; —CN; —CNO; —C(O)R$^{13}$; —C(O)OR$^{13}$; —C(O)NR$^{11}$R$^{12}$; —C(R$^{13}$)$_z$H$_{(3-z)}$; —NR$^{11}$R$^{12}$; —NR$^{11}$C(O)R$^{10}$; —NR$^{11}$C(O)OR$^{10}$; —NCO; —NR$^{12}$SO$_2$R$^{13}$; —S(O)$_x$R$^{13}$; —S(O)$_2$NR$^{11}$R$^{12}$; —NO$_2$; —N$_3$; —(CH$_2$)$_k$R$^{14}$; —(CH$_2$)$_k$—Z—R$^{16}$; and —(CH$_2$)$_k$—Z—(CH$_2$)$_m$—R$^{14}$; and L, M, R$^{10}$, R$^{11}$, R$^{12}$, R$^{13}$, R$^{14}$, R$^{16}$, Z, k, m, x, and z are as defined above.

In some embodiments, $R^2$ and $R^3$, and $R^{2'}$ and $R^{3'}$ may optionally be taken together with the carbon atoms to which they are attached to form one or more rings which may in turn be substituted with one or more R$^{20}$ groups. In certain embodiments, $R^2$ and $R^3$, and $R^{2'}$ and $R^{3'}$ may optionally be taken together with the carbon atoms to which they are attached to form phenyl substituted with one or more R$^{20}$ groups. In certain embodiments, $R^2$ and $R^3$, and $R^{2'}$ and $R^{3'}$ may optionally be taken together with the carbon atoms to which they are attached to form phenyl substituted with one or more $C_{1-12}$ alkyl groups.

In certain embodiments, $R^2$ and $R^3$, and $R^{2'}$ and $R^{3'}$ are both of formula:

In some embodiments, $R^4$ is of formula:

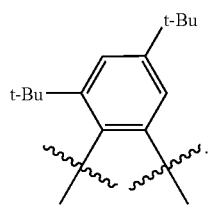 [SMILES: *c1cc(C(C)(C)C)cc(C(C)(C)C)c1*]

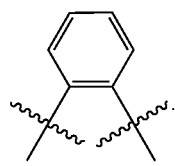 [SMILES: *c1ccccc1*]

In some embodiments, a Lewis acid of the carbonylation catalyst is of formula IIIb, wherein M is Al or Cr. In some embodiments, a Lewis acid of the carbonylation catalyst is of formula IIIb, wherein L is a solvent. In certain embodiments, a Lewis acid of the carbonylation catalyst is of formula IIIb and L is an ethereal solvent. In certain embodiments, a Lewis acid of the carbonylation catalyst is of formula IIIb and each L is THF.

In some embodiments, a Lewis acid of the carbonylation catalyst is of formula IIIb(i):

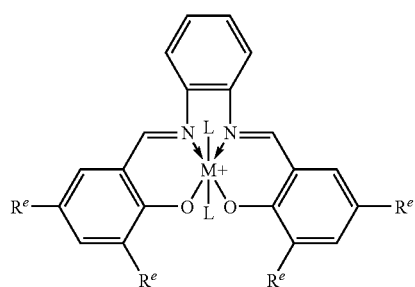

IIIb(i)

wherein L, M, and $R^e$ are as defined above and herein.

In some embodiments, a Lewis acid of the carbonylation catalyst is of formula IIIb(i), wherein L is a solvent. In certain embodiments, a Lewis acid of the carbonylation catalyst is of formula IIIb(i) and L is an ethereal solvent. In certain embodiments, a Lewis acid of the carbonylation catalyst is of formula IIIb(i) and each L is THF. In certain embodiments, wherein a Lewis acid of the carbonylation catalyst is of formula IIIb(i), the transition metal complex is $[Co(CO)_4]^-$. In certain embodiments, wherein a Lewis acid of the carbonylation catalyst is of formula IIIb(i), each $R^e$ is independently $C_1$-$C_6$ alkyl. In certain embodiments, wherein a Lewis acid of the carbonylation catalyst is of formula IIIb(i), each $R^e$ is t-butyl. In some embodiments, a Lewis acid of the carbonylation catalyst is of formula IIIb(i), wherein M is Al or Cr.

In certain embodiments, a carbonylation catalyst is of formula IIb(i):

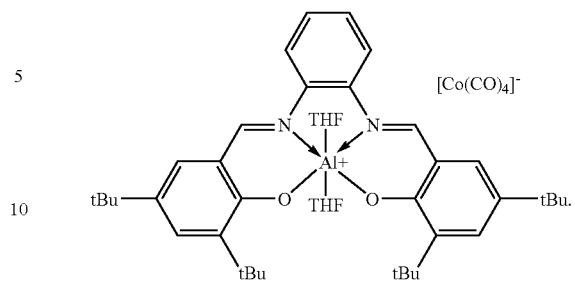

IIb(i)

In certain embodiments, a carbonylation catalyst is of formula IIb(ii):

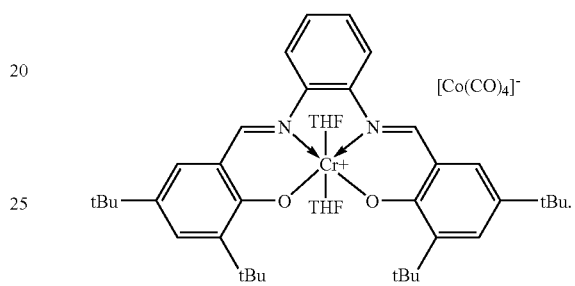

IIb(ii)

In some embodiments, a Lewis acid of a carbonylation catalyst is of formula IIIc:

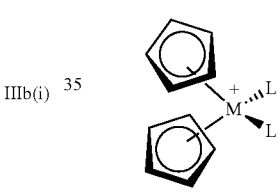

IIIc wherein L and M are as defined above and herein.

In some embodiments, a Lewis acid of the carbonylation catalyst is of formula IIIc, wherein L is a solvent. In certain embodiments, a Lewis acid of the carbonylation catalyst is of formula IIIc and L is an ethereal solvent. In certain embodiments, a Lewis acid of the carbonylation catalyst is of formula IIIc and each L is THF. In certain embodiments, wherein a Lewis acid of the carbonylation catalyst is of formula IIIc, M is Ti. In certain embodiments, wherein a Lewis acid of the carbonylation catalyst is of formula Inc, the transition metal complex is $[Co(CO)_4]^-$.

In certain embodiments, a carbonylation catalyst is of formula IIc(i):

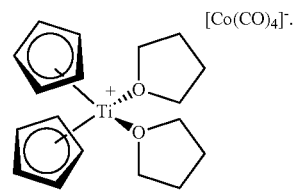

IIc(i)

Reaction Conditions

Turning now to a more detailed description of the invention, it has been found that the catalyst described above can be used to successfully transform epoxides into 3-hydroxy-δ-lactones exclusively, with no or very little formation of the competing β-lactone product. In various embodiments, certain reaction conditions may affect the outcome (e.g., the yield) of these processes including, but not limited to: the presence of a solvent, the concentration of the substrate, the amount of catalyst present, and the pressure and temperature at which the reaction is performed.

In certain embodiments, the solvent used will fully dissolve the epoxide substrate and provide a reaction mixture in which the catalyst employed is at least partially soluble. Suitable solvents may include ethers, ketones, aromatic hydrocarbons, halocarbons, esters, nitriles, and some alcohols. For example, without limitation, a suitable solvent may include: 1,4-dioxane; tetrahydrofuran; tetrahydropyran; dimethoxyethane; glyme; diethyl ether; t-butyl methyl ether; 2,5-dimethyl tetrahydrofuran; ethyl acetate; propyl acetate; butyl acetate; acetone; 2-butanone; cyclohexanone; toluene; acetonitrile; and difluorobenzene. Mixtures of two or more of the above solvents are also useful, and in some cases may be preferred to a single solvent.

In certain embodiments, the solvent is a polar aprotic solvent such as dimethoxyethane. In some embodiments, the amount of solvent used is such that the concentration of the reaction is between approximately 0.1 M and approximately 10 M. In some embodiments, the concentration is between approximately 0.1 M and approximately 5 M. In some embodiments, the concentration is between approximately 0.1 M and approximately 2.5 M. In some embodiments, the concentration is between approximately 0.5 M and approximately 5 M. In some embodiments, the concentration is between approximately 0.5 M and approximately 1.5 M. In certain embodiments, the concentration is approximately 1.0 M.

The reaction of the present invention is conducted under a carbon monoxide atmosphere at a pressure from about 40 psi, to about 2500 psi. For example the carbon monoxide pressure may range from about 80 psi to about 2000 psi or from about 500 psi to about 1000 psi. In certain embodiments, the carbon monoxide pressure is approximately 800 psi. Optionally, the atmosphere under which the reaction is conducted can include other gasses. Such other gasses can include, for example, hydrogen, methane, nitrogen, carbon dioxide, air, and trace amounts of steam. The present invention also specifically encompasses processes in which other carbon monoxide-containing gas streams provide the atmosphere under which the reaction is conducted, the use of syngas, wood gas, or other carbon monoxide-containing industrial gas streams are specifically included.

Turning next to the effect of temperature, in certain embodiments the reaction temperature was found to affect the rate and outcome of processes of the invention. At higher temperatures the reaction may proceed more quickly than at lower temperatures, but the propensity to form reaction by-products may increase. In some cases therefore, the optimal temperature will be dependent upon the pressure at which the reaction is conducted. When the reaction is conducted at a carbon monoxide pressure of about 800 psi, the optimal temperature ranges from approximately 0° C. to approximately 200° C. In some embodiments, the temperature ranges from approximately 5° C. and approximately 150° C. In some embodiments, the temperature ranges from approximately 10° C. to approximately 100° C. In certain embodiments, the temperature ranges from approximately 25° C. and approximately 75° C. In some embodiments, the optimal reaction temperature is approximately 60° C. In some embodiments, the optimal reaction temperature is approximately 70° C. In some embodiments, the optimal reaction temperature is approximately 80° C.

The reaction time of the inventive method ranges from approximately 1 minute to approximately 1 week. In some embodiments, the reaction time ranges from approximately 0.5 hour to approximately 140 hours. In some embodiments, the reaction time ranges from approximately 1.0 hour to approximately 96 hours. In some embodiments, the reaction time ranges from approximately 1.0 hour to approximately 72 hours. In some embodiments, the reaction time ranges from approximately 6 hours to approximately 72 hours. In some embodiments, the reaction time ranges from approximately 12 hours to approximately 72 hours. In some embodiments, the reaction time ranges from approximately 12 hours to approximately 48 hours. In some embodiments, the reaction time ranges from approximately 12 hours to approximately 36 hours. In certain embodiments, the reaction time is approximately 6 hours. In certain embodiments, the reaction time is approximately 12 hours. In certain embodiments, the reaction time is approximately 18 hours. In certain embodiments, the reaction time is approximately 24 hours. In certain embodiments, the reaction time is approximately 48 hours.

Turning next to the catalysts, the catalyst is preferably present in an amount sufficient to allow the reaction process to be completed in a convenient time interval. In real terms this can require catalyst loadings ranging from about 0.0001 mole percent to about 20 mole percent based on the epoxide substrate. In certain embodiments, the catalyst loading can range from about 0.001 mole percent to about 20 mole percent. In certain embodiments, the catalyst loading can range from about 0.001 mole percent to about 10 mole percent. In certain embodiments, the catalyst loading can range from about 0.01 mole percent to about 10 mole percent. In certain embodiments, the catalyst loading can range from about 0.1 mole percent to about 10 mole percent. In certain embodiments, the catalyst loading can range from about 0.1 mole percent to about 5 mole percent. In certain embodiments, the catalyst loading can range from about 0.5 mole percent to about 2.5 mole percent. In certain embodiments, the catalyst loading can range from about 1.0 mole percent to about 2.0 mole percent. In certain embodiments, the catalyst loading is about 2.0 mole percent.

The catalysts of the instant invention can be prepared in any one of the methods known to those of ordinary skill in the art. In certain embodiments wherein the catalyst is $HCo(CO)_4$, preparation of the catalyst proceeds by treating $Ph_3Si(CO)_4$ with p-toluenesulfonic acid (PTSA) in a suitable solvent (e.g., dimethoxyethane [DME]).

DEFINITIONS

Alkenyl: The term 'alkenyl' as used herein means a branched or unbranched, mono- or poly-unsaturated hydrocarbon radical having one or more carbon-carbon double bonds. Each double bond can be substituted or unsubstituted, and can have cis or trans stereochemistry. The double bonds of polyunsaturated radicals can be conjugated or unconjugated and can include allenes. The term is also meant to encompass alkenyl groups where one or more hydrogen atoms are replaced by a halogen atom. Examples of alkenyl groups include, but are not limited to: vinyl, allyl, isoprenyl, cis-hex-3-enyl, trans-hex-3-enyl, trans, trans butane-1,3-dienyl, 3,3 dimethyl allenyl, 4-methyl hex-1-enyl, cis-but-2-enyl, and 4-methyl-1-hexenyl.

Alkyl: The term 'alkyl' as used herein means a branched or straight chain saturated hydrocarbon radical. The term is also meant to encompass alkyl groups where one or more hydrogen atoms are replaced by a halogen atom. Examples of alkyl groups include, but are not limited to: methyl, ethyl, n-propyl, n-hexyl, isobutyl, t-butyl, thexyl, 2-methyl pentyl, dichloromethyl, fluoromethyl, trifluoromethyl, pentafluoropropyl, and n-decyl.

Alkynyl: The term 'alkynyl' as used herein means a branched or unbranched, mono- or poly-unsaturated hydrocarbon radical having one or more carbon-carbon triple bonds. The term is also meant to encompass alkenyl groups where one or more hydrogen atoms are replaced by a halogen atom. Examples of alkynes include, but are not limited to propargyl, 2-butynyl, 5-hexynyl, and 2,2-dimethyl-3-butynyl.

Carbocycle: The term 'carbocycle' as used herein means a saturated, unsaturated or aromatic ring system where all atoms comprising the ring(s) are carbon atoms. The term includes structures having more than one ring, such as fused ring systems, bridged ring systems and spirocycles. Carbocycles can include the carbon atoms of keto, imine, and oxime groups and can be substituted with one or more additional groups. If a specific number of carbons is recited with a specific appearance of the term carbocycle (e.g., 'up to $C_{12}$ carbocycle'), it is to be understood that the number refers only to those carbon atoms comprising the ring system and does not include any carbon atoms in substituents that may optionally be attached thereto.

Where a substituent is defined to encompass alkenyl or alkynyl substituents, it is to be understood that moieties having both carbon-carbon double bonds and carbon-carbon triple bonds (e.g., enynes) are also encompassed.

Heterocycle: The term 'heterocycle' as used herein means a saturated, unsaturated, or aromatic ring structure where one or more atoms in the ring is a heteroatom. The term includes structures having more than one ring, such as fused ring systems, bridged ring systems and spirocycles. The rings can also include the carbon atoms of keto, imine, and oxime groups and can be substituted with one or more additional groups. If a specific number of carbons is recited with a specific appearance of the term heterocycle (e.g., 'up to $C_{12}$ heterocycle'), it is to be understood that the number refers only to those carbon atoms comprising the ring system and does not include any carbon atoms in substituents that may optionally be attached thereto.

The present invention will be more specifically illustrated with reference to the following examples. Many of these examples are described in Rowley et al., *J. Am. Chem. Soc.* 2007, (129) 4948-4960 and in the supporting information published therewith. The entirety of this publication and its supporting information are hereby incorporated herein by reference.

EXAMPLES

General Considerations

All manipulations of air- and/or water-sensitive compounds were carried out using standard Schlenk line techniques or in an MBraun Unilab drybox under an atmosphere of dry nitrogen. NMR spectra were recorded using Varian Mercury or Inova spectrometers ($^1$H NMR, 300 MHz; $^{13}$C NMR, 75 MHz and 125 MHz; $^{19}$F NMR, 470 MHz) and referenced against residual solvent shifts for $^1$H and $^{13}$C NMR and hexafluorobenzene for $^{19}$F NMR spectra. $^1$H NMR and $^{13}$C NMR spectra of the product $^3$HLs were identified by comparison to published spectra for 4-hydroxy-6-pentyl-δ-lactone (7),[1] 4-hydroxy-6-methyl-δ-lactone (7a),[2] 4-hydroxy-6-phenyl-δ-lactone (7c),[3] 6-ethyl-4-hydroxy-6-methyl-δ-lactone (7d),[4] 6-(tert-butyldimethylsiloxymethyl)-4-hydroxy-δ-lactone (7i),[5] and 6-chloromethyl-4-hydroxy-δ-lactone (7j).[6] All epoxides and lactones were prepared as racemic mixtures of diastereomers, except where noted. Mass spectra were acquired using a JEOL GCMate II mass spectrometer operating at 3000 resolving power for high resolution measurements in positive ion mode and an electron ionization potential of 70 eV. Samples were introduced via a GC inlet using an Agilent HP 6890N GC equipped with a 30 m (0.25 μm i.d.) HP-5 ms capillary GC column. The carrier gas was helium with a flow rate of 1 ml/min. Samples were introduced into the GC using a split/splitless injector at 230° C. with a split ratio of 10:1. Lactones 7b, (R,R)-7b, 7g, and 7h were analyzed using direct injection into the mass spectrometer to avoid dehydration in the GC. Optical rotations were measured on a Perkin-Elmer 241 digital polarimeter and are reported in the following format: $[\alpha]^T_D r$ (c, solvent), where T=temperature in ° C., D refers to the sodium D line (589 nm), r is the measured rotation, and c is the concentration in g/dL. IR spectra were measured on a Mattson RS-10500 Research Series FTIR. In situ IR data were collected using a 100-mL Parr reactor modified for use with a Mettler-Toledo ReactIR 4000 Reaction Analysis System fitted with a Sentinel DiComp high-pressure probe, and analyzed with ReactIR software version 2.21. All other carbonylation reactions were performed in a custom-built six-well reactor[7] heated on a hot plate and equipped with magnetic stir bars. All carbonylation reactions were performed in a well-ventilated fume hood equipped with a CO sensor, as carbon monoxide is a highly toxic gas.

Materials

Tetrahydrofuran (THF) was dried over a column of alumina and degassed by sparging with dry nitrogen. Diethyl ether was dried and deoxygenated on columns of alumina and Q5 copper, respectively. 1,2-Dimethoxyethane (DME) was transferred under reduced pressure from sodium/benzophenone. 1,2-Epoxyhexane, 1,1,2,2-tetrafluoroethylglycidyl ether, epichlorohydrin, tert-butyldimethylsilylglycidyl ether, hexanal, cyclopentanone, cyclododecanone, 4-pentene-2-ol, 4-phenyl-1-buten-4-ol, allyl magnesium bromide, vinyl magnesium bromide, copper iodide, meta-chloroperbenzoic acid (mCPBA), and peracetic acid were purchased from Aldrich and used as received. Sodium acetate (anhydrous), 2-butanone, and acetic acid were purchased from Mallinckrodt. 1,6-Heptadien-4-ol was purchased from Acros. para-Toluene sulfonic acid was purchased from Fischer. Dicobalt octacarbonyl and (1R,2R)-(−)-1,2-cyclohexanediamino-N,N'-bis(3,5-di-t-butylsalicylidene)cobalt were purchased from Strem. Research-grade carbon monoxide (99.99% min.) was purchased from Matheson and used without purification. Catalysts 1,[8] 2,[9] 3,[10] 4,[11] and 5[12] and Ph$_3$SiCo(CO)$_4$[13] were prepared according to literature procedures. 4-Hydroxy-1,2-epoxynonane (6),[14] 4-hydroxy-1,2-epoxypentane (6a),[15] 4-hydroxy-4-phenyl epoxybutane (6c),[16] 4-hydroxy-4-methyl-1,2-epoxyhexane (6d),[17] 1-(2,3-epoxypropyl)-cyclopentan-1-ol (6e),[18] and 4-hydroxy-1,6-heptadiene monoepoxide (6g)[19] were synthesized in an analogous manner to those in the Experimental Section and characterized by comparison to literature reports. Solid epoxides were dried under vacuum and liquid epoxides were dried over activated 4 Å molecular sieves and degassed three times by freeze-pump-thaw cycles.

The following examples describe exemplary catalyst/solvent combinations which we have shown can be used to effect high yield double carbonylation of epoxides. It is to be understood that these combinations are exemplary and that, in view of the representative teachings that are provided in this disclosure, those skilled in the art will be able to identify a variety of alternative combinations.

Example 1

Convergent Synthesis of Homoglycidols

This example describes the synthesis of various glycidols from commercially available epoxides and aldehydes (Scheme shown below).

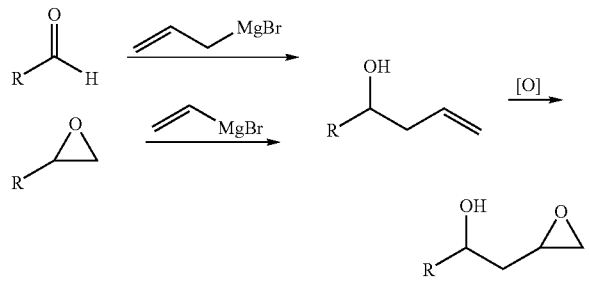

4-Hydroxy-1,2-epoxyoctane (6b)

Copper iodide (0.79 g, 4.1 mmol) was added to a 250-mL oven-dried three-neck round-bottom flask and diluted with 40 mL dry THF. Vinyl magnesium bromide (1.0 M solution in diethyl ether, 50 mL, 50 mmol) was slowly added to the flask and stirred for 20 minutes. The flask was then cooled to −78° C. and a solution of 1,2-epoxyhexane (4.15 g, 41 mmol) in 30 mL THF was slowly added via an addition funnel under nitrogen. The reaction was slowly warmed to room temperature over the course of 16 hours, then cooled to 0° C. and quenched with saturated ammonium chloride. The aqueous layer was extracted with diethyl ether and the combined organic layers were evaporated in vacuo.

The crude homoallylic alcohol was epoxidized by diluting in $CH_2Cl_2$ (~1 M solution) and slowly adding mCPBA (11 g, 66 mmol) to the solution at 0° C. The reaction was warmed to room temperature and stirred for 18 hours, at which time it was cooled back to 0° C. and quenched with 10% sodium bisulfate (aq). The organic layer was extracted twice with sat. $NaHCO_3$ (aq) and sat. NaCl (aq) and dried over $MgSO_4$. Solvent was removed in vacuo and the crude epoxide was distilled at 65° C. under vacuum to afford pure 6b (1.8 g, 34%, syn:anti ca. 50:50) as a racemic mixture of diastereomers. $^1$H NMR (δ, $CDCl_3$, 300 MHz) 0.85 (t, $^3J$=6.5 Hz, 6H), 1.18-1.59 (m, 12H), 1.70-1.82 (m, 2H), 2.38-2.58 (m, 4H), 2.70-2.80 (m, 2H), 3.00-3.15 (m, 2H), 3.69-3.87 (m, 2H); $^{13}$C NMR (δ, $CDCl_3$, 75 MHz) 14.15, 22.78, 27.79, 27.85, 37.25, 37.43, 39.35, 39.87, 46.75, 47.12, 50.38, 50.72, 69.30, 70.44.

1-(2,3-Epoxypropyl)-cyclododecan-1-ol (6f)

An oven-dried 500-mL three-neck round-bottom flask was charged with cyclododecanone (6.00 g, 32.9 mmol) and 50 mL dry THF. A 100-mL addition funnel with allyl magnesium bromide (1.0 M solution in THF, 36.2 mL, 36.2 mmol) was attached and the flask was cooled in an ice bath for 10 minutes. The Grignard was slowly dripped in over the course of 30 minutes while stirring at 0° C. under nitrogen. After addition, the ice bath was removed and the reaction mixture was stirred for 4 hours at room temperature under nitrogen. Excess Grignard was quenched by slowly adding water to the reaction mixture cooled to 0° C., and the product was extracted three times with diethyl ether. The organic layer was dried over $Na_2SO_4$ and solvent was removed under vacuum to obtain the homoallylic alcohol that was used without further purification.

The epoxide was synthesized by addition of peracetic acid (32% solution in dilute acetic acid, 16.6 ml, 79.0 mmol) to a $CH_2Cl_2$ solution of crude homoallylic alcohol and sodium acetate (4.05 g, 49.4 mmol) at 0° C.; the reaction was stirred at room temperature for 18 h. Excess peroxide was quenched with a 10% aqueous solution of sodium bisulfite and the organic layer was washed 3 times with water and brine. Evaporation of solvent yielded crude epoxide which was recrystallized from hot hexanes (5 mL) to afford colorless crystals of 6f (5.03 g, 64%) as a racemic mixture. $^1$H NMR (δ, $CDCl_3$, 300 MHz) 1.22-1.86 (m, 25H), 2.48 (dd, $^3J$=2.8 Hz, $^2J$=5.1 Hz, 1H), 2.80 (dd, $^3J$=3.9 Hz, $^2J$=5.1 Hz, 1H), 3.19 (dddd, $^3J$=2.7 Hz, $^3J$=3.0 Hz, $^3J$=4.2 Hz, $^3J$=5.1 Hz, 1H); $^{13}$C NMR (δ, $CDCl_3$, 75 MHz) 19.59, 19.80, 22.24, 22.71, 26.18, 26.56, 26.60, 34.91, 35.05, 43.25, 46.99, 49.24, 75.47. Note: Two peaks were not visible due to degeneracy.

5-(1,1,2,2-Tetrafluoroethoxy)-4-hydroxy-1,2-epoxypentane (6h)

Copper iodide (0.52 g, 2.7 mmol) was added to a 250-mL oven-dried three-neck round-bottom flask and diluted with 25 mL dry THF. Vinyl magnesium bromide (1.0 M solution in diethyl ether, 27 mL, 27 mmol) was slowly added to the flask and stirred for 20 minutes. The flask was then cooled to −78° C. and a solution of 1,1,2,2-tetrafluoroethyl glycidyl ether (5.2 g, 30 mmol) in 20 mL THF was slowly added via an addition funnel under nitrogen. The reaction was slowly warmed to room temperature over the course of 16 hours, then cooled to 0° C. and quenched with saturated ammonium chloride. The aqueous layer was extracted with diethyl ether and the combined organic layers were evaporated in vacuo.

The crude homoallylic alcohol was epoxidized by diluting in $CH_2Cl_2$ (~1 M solution) and slowly adding mCPBA (8.5 g, 49 mmol) to the solution at 0° C. The reaction was warmed to room temperature and stirred for 18 hours, at which time it was cooled back to 0° C. and quenched with 10% sodium bisulfate (aq). The organic layer was extracted twice with sat. $NaHCO_3$ (aq) and sat. NaCl (aq) and dried over $MgSO_4$. Solvent was removed in vacuo and the crude epoxide was distilled at 60° C. under vacuum to afford pure 6h (2.2 g, 33%, syn: anti ca. 50:50) as a racemic mixture of diastereomers. NMR (δ, $CDCl_3$, 300 MHz) 1.49-1.65 (m, 2H), 1.94-2.05 (m, 1H), 2.40 (d, $^3J$=3.8 Hz, 1H), 2.55 (dd, $^3J$=2.7 Hz, $^3J$=4.8 Hz, 1H), 2.61 (dd, $^3J$=2.7 Hz, $^3J$=4.8 Hz, 1H), 2.82 (dd, $^3J$=4.1 Hz, $^3J$=4.7 Hz, 1H), 2.86 (dd, $^3J$=4.1 Hz, $^3J$=4.7 Hz, 1H), 3.10-3.20 (m, 2H), 3.91 (dd, $^3J$=7.0 Hz, $^2J$=10.0 Hz, 1H), 4.00 (pseudo-d, 2H), 4.04 (dd, $^3J$=3.9 Hz, $^2J$=10.0 Hz, 1H), 4.07-4.20 (m, 2H), 5.74 (tt, $^3J$=2.5 Hz, $^2J$=53.3 Hz, 2H); $^{13}$C NMR (δ, $CDCl_3$, 75 MHz) δ5.55, 35.82, 46.77, 47.25, 49.60, 49.72, 67.54, 67.91 (t, $^3J$=4.6 Hz), 68.14, 68.15 (t, $^3J$=4.6 Hz), 107.87 (tt, $^2J$=42 Hz, J=249 Hz) Note: The $CF_2$ carbon was not definitively identified.

5-(tert-Butyldimethylsilyloxy)-4-hydroxy-1,2-epoxypentane (6i)

Copper iodide (0.36 g, 1.9 mmol) was added to a 250-mL oven-dried three-neck round-bottom flask and diluted with 20 mL dry THF. Vinyl magnesium bromide (1.0 M solution in diethyl ether, 23 mL, 23 mmol) was slowly added to the flask and stirred for 20 minutes. The flask was then cooled to −78° C. and a solution of tert-butyldimethylsilyl glycidyl ether (3.6 g, 19 mmol) in 10 mL THF was slowly added via an addition funnel under nitrogen. The reaction was slowly warmed to room temperature over the course of 16 hours, then cooled to 0° C. and quenched with sat. NH$_4$Cl (aq). The aqueous layer was extracted with diethyl ether and the combined organic layers were evaporated in vacuo.

The epoxide was synthesized by addition of peracetic acid (32% solution in dilute acetic acid, 9.6 mL, 46 mmol) to a CH$_2$Cl$_2$ solution of crude homoallylic alcohol and sodium acetate (2.3 g, 28 mmol) at 0° C.; the reaction was stirred at room temperature for 18 h. Excess peroxide was quenched with 10% sodium bisulfate (aq) and the organic layer was washed 3 times with water and brine. Evaporation of solvent yielded crude epoxide which was purified by column chromatography with 30% ethyl acetate in hexanes to afford 6i (2.5 g, 58%, syn:anti ca. 50:50) as a racemic mixture of diastereomers. $^1$H NMR (δ, CDCl$_3$, 300 MHz) 0.035 (s, 12H), 0.86 (s, 18H), 1.37-1.83 (m, 4H), 2.46-2.51 (m, 2H), 2.63 (d, $^3$J=3.6 Hz, 1H), 2.67 (d, $^3$J=3.6 Hz, 1H), 2.73 (t, $^3$J=4.8, 1H), 2.77 (t, $^3$J=4.8 Hz, 1H), 3.02-3.12 (m, 2H), 3.37-3.66 (m, 4H), 3.75-3.90 (m, 2H); $^{13}$C NMR (δ, CDCl$_3$, 75 MHz) −5.28, −5.24, 18.40, 25.99, 35.83, 36.16, 46.83, 47.32, 49.84, 49.94, 66.91, 67.23, 69.88, 69.98.

5-Chloro-4-hydroxy-1,2-epoxypentane (6j)

Copper iodide (2.3 g, 12 mmol) was added to a 500-mL oven-dried three-neck round-bottom flask and diluted with 100 mL dry THF. Epicholorohydrin (12 g, 130 mmol) was added to the flask which was equipped with an addition funnel and cooled to −78° C. Vinyl magnesium bromide (1.0 M solution in diethyl ether, 120 mL, 120 mmol) was slowly added to the flask and stirred for 30 minutes, then warmed to room temperature and stirred for 16 hours. The reaction was cooled to 0° C. and quenched with sat. NH$_4$Cl (aq). The organic layer was pushed through a plug of silica to remove magnesium salts and excess epichlorohydrin was removed in vacuo.

The homoallylic alcohol was epoxidized with peracetic acid as in 6i. The crude epoxide was purified by column chromatography using 30% ethyl acetate in hexanes to afford 6j (2.5 g, 15%, syn:anti ca. 50:50) as a racemic mixture of diastereomers. $^1$H NMR (δ, CDCl$_3$, 300 MHz) 1.43-1.69 (m, 2H), 1.87-2.00 (m, 2H), 2.49 (dd, $^3$J=2.7 Hz, 2J=4.8 Hz, 1H), 2.53 (dd, $^3$J=3.0 Hz, $^2$J=4.8 Hz, 1H), 2.75 (t, $^3$J=4.5 Hz, 1H), 2.79 (t, $^3$J=4.5 Hz, 1H), 3.02-3.13 (m, 2H), 3.09 (d, $^3$J=4.8, 1H), 3.16 (d, $^3$J=4.8 Hz, 1H), 3.41-3.63 (m, 4H), 3.93-4.07 (m, 2H); $^{13}$C NMR (δ, CDCl$_3$, 75 MHz) δ6.83, 36.95, 46.67, 47.28, 49.56, 49.66, 49.69, 49.83, 69.35, 69.71.

(2R,4R)-4-Hydroxy-1,2-epoxyoctane ((R,R)-6b)

(R)-1,2-Epoxyhexane was prepared as reported by Jacobsen and coworkers (Schaus, et al., *J. Am. Chem. Soc.* 2002, 124, 1307-1315). Ring opening of the optically pure epoxide by vinyl magnesium bromide followed by epoxidation with mCPBA were performed in an analogous manner as 6h to give a 1:1 mixture of diastereomers. The diastereomers were resolved using Jacobsen HKR conditions. The epoxide (2.67 g, 18.5 mmol) was diluted in 2.5 mL THF. To this solution was added (1R,2R)-(−)-1,2-cyclohexanediamino-N,N'-bis(3,5-di-tbutylsalicylidene)cobalt (56.2 mg, 0.93 mmol) and glacial acetic acid (21.2 μL, 0.37 mmol). The solution was cooled to 0° C. and water (183 μL 10.2 mmol) was added dropwise. After stirring at room temperature for 24 hours, THF was removed in vacuo and the residue was distilled under vacuum at 65° C. to afford (R,R)-6b (1.18 g, 13% from racemic 1,2-epoxyhexane, >99:1 syn:anti) as a colorless oil. $^1$H NMR (δ, CDCl$_3$, 300 MHz) 0.85 (t, $^3$J=6.9 Hz, 3H), 1.17-1.81 (m, 8H), 2.42-2.49 (m, 1H), 2.47 (d, $^3$J=4.2 Hz, 1H), 2.72 (t, $^3$J=4.2 Hz, 1H), 2.99-3.07 (m, 1H), 3.74-3.86 (m, 1H); $^{13}$C NMR (δ, CDCl$_3$, 75 MHz) 14.13, 22.75, 27.77, 37.22, 39.84, 46.73, 50.69, 70.38.

Example 2

Preparation of HCo(CO)$_4$

This procedure was adapted from a similar synthesis of HCo(CO)$_4$ (Byrne et al. *Manuscript in Preparation*). In the glove box, Ph$_3$SiCo(CO)$_4$ (0.12 mmol) and p-toluenesulfonic acid (0.12 mmol) were weighed into separate flame-dried vials. DME (6.0 mL) was divided evenly into each vial to completely dissolve the catalyst components. The two solutions were combined to form a colorless solution of HCo(CO)$_4$ (0.05 M in DME) which was used immediately. Note: HCo(CO)$_4$ must be used immediately after preparation to ensure reproducible catalytic activity.

Example 3

Catalyst Screening for 3HL Formation

Table 1 illustrates initial results to carbonylate 4-hydroxy-1,2-epoxynonane (6) to d-lactone (7) using known epoxide carbonylation catalysts. Reactions using chromium catalysts 1 and 3 afforded largely the β-lactone product, whereas aluminum catalysts 2 and 4, and titanium catalyst 5 led to preferential formation of δ-lactone. Notably, HCo(CO)$_4$ led to virtually exclusive formation of the δ-lactone.

TABLE 1

Catalyst Screening for 3HL Formation

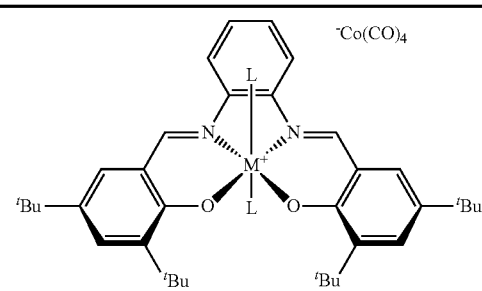

L = THF

M = Cr; 1
M = Al; 2

TABLE 1-continued

Catalyst Screening for 3HL Formation

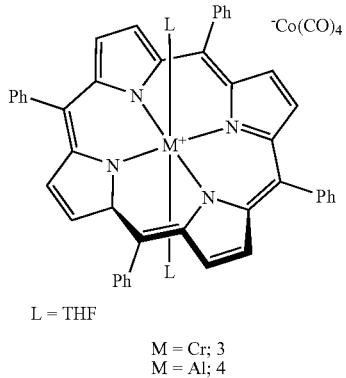

L = THF

M = Cr; 3
M = Al; 4

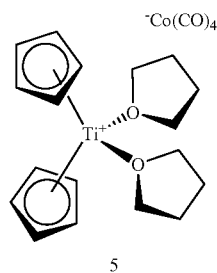

5

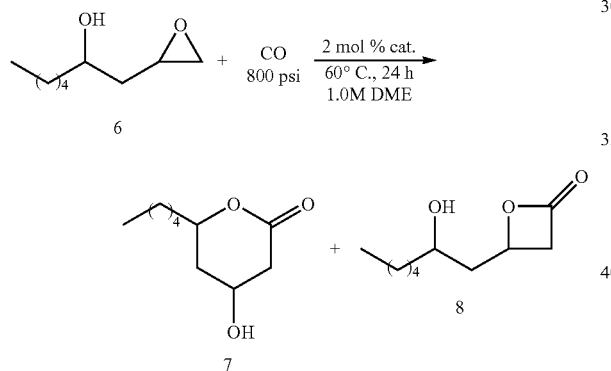

| entry | catalyst | conversion[a] (%) δ-lactone (7) | β-lactone (8) |
|---|---|---|---|
| 1 | 1 | 16 | 84 |
| 2 | 2 | 73 | 27 |
| 3 | 3 | 33 | 67 |
| 4 | 4 | 58 | 42 |
| 5 | 5 | 83 | 17 |
| 6 | Co$_2$(CO)$_8$ | 67 | 33 |
| 7 | HCo(CO)$_4$[b] | >99 | ND[c] |

[a]Conversions determined by $^1$H NMR spectroscopy; diastereomeric ratios of 6, 7, and 8 ca. 1:1.
[b]Prepared in situ; see supporting information for details
[c]ND = Not Detected.

Example 4

Carbonylation of Homoglycidols

In a custom-built, six-well, high pressure stainless steel reactor, six oven-dried vials (8 mL) were charged with epoxide (1.0 mmol) and magnetic stir bars. Freshly prepared HCo(CO)$_4$ solution (1.0 mL, 0.05 M in DME) was transferred to each vial via syringe. The reactor was then sealed, pressured to 800 psi CO, and heated at 60° C. for 24 hours while stirring. After the reaction time, the reactor was cooled in dry ice for 10 minutes and the wells were vented in a well-ventilated fume hood. Crude $^1$H NMR spectra were obtained by removing an aliquot of reaction mixture and passing it through a plug of silica with CDCl$_3$. Reactions that cleanly produced δ-lactone were purified by chromatography. The crude reaction mixture was concentrated to an oil under vacuum. This crude product was passed through silica gel, first using 30% ethyl acetate in hexanes to remove catalyst residue, then with 70% ethyl acetate in hexanes to elute the δ-lactone product. On a small scale, the isolated 3HLs were sometimes contaminated with small amounts (<5%) of catalyst residue. The contamination was most dramatic with the alkyl-substituted homoglycidols (7-7b), leading to lower isolated yields. The product 3HL was obtained by removing solvent in vacuo and analyzed by comparison to literature reports, or fully characterized in the case of unreported compounds.

Example 5

Optimization of Carbonylation Conditions

Using the above general procedure for homoglycidol carbonylation by HCo(CO)$_4$, CO pressure, temperature, catalyst loading, and reaction time were varied to determine the optimal conditions (Table S1).

TABLE S1

Optimization of Carbonylation conditions.

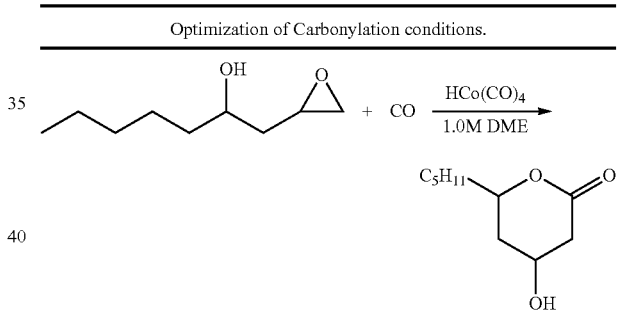

| Entry | Epoxide:Catalyst | CO Pressure (psi) | Time (h) | Temperature (° C.) | Conversion[a] (%) |
|---|---|---|---|---|---|
| 1 | 20:1 | 100 | 48 | 23 | 47 |
| 2 | 20:1 | 800 | 6 | 60 | 99 |
| 3 | 20:1 | 800 | 6 | 80 | 99[b] |
| 4 | 50:1 | 800 | 24 | 60 | 99 |
| 5 | 100:1 | 800 | 24 | 60 | 30 |
| 6 | 200:1 | 800 | 24 | 60 | NR[c] |

[a]Conversions determined by $^1$H NMR spectroscopy.
[b]Product contaminated with unknown impurities.
[c]NR = No Reaction; only starting material detected.

Example 6

Synthesis of 3HLs Using HCo(CO)$_4$

Once reaction conditions were optimized for efficient δ-lactone formation, a variety of substituted homoglycidols were carbonylated (Table 2). Both alkyl- and aryl-substituted homoglycidols were carbonylated cleanly to 3HLs. Disubstituted homoglycidols (entries 4-6) produced 7d and the spiro 3HLs 7e and 7f; however, a small amount of β-lactone was also formed in these carbonylations.

TABLE 2
Synthesis of 3HLs using HCo(CO)₄
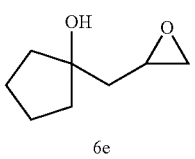
| | epoxide | | | | |
|---|---|---|---|---|---|
| entry | R | R' | | δ-lactone | yield[a] (%) |
| 1 | Me | H | 6a | 7a | 73 |
| 2 | "Bu | H | 6b | 7b | 60 |
| 3 | Ph | H | 6c | 7c | 81 |
| 4 | Me | Et | 6d | 7d | 58[b] |
| 5 | 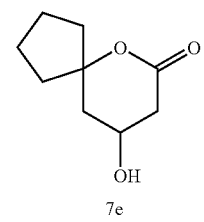<br>6e | 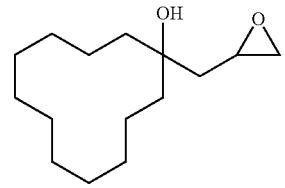<br>7e | 67[c] |
|---|---|---|---|
| 6 | 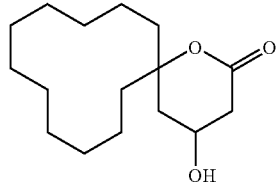<br>6f | 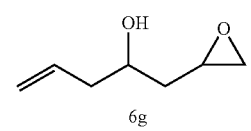<br>7f | 75[c] |
| 7[d] | 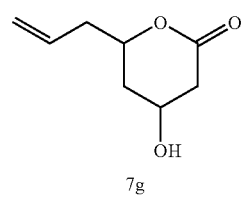<br>6g | 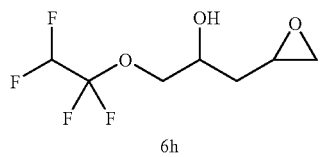 [SMILES: OC(COC(F)(F)C(F)F)CC1CO1]<br>7g | 76 |
| 8[d] | 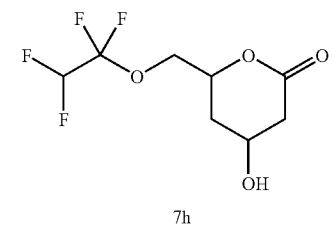 [SMILES: O=C1CC(O)CC(COC(F)(F)C(F)F)O1]<br>6h | 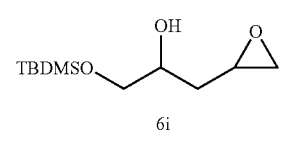 [SMILES: CC(C)(C)[Si](C)(C)OCC(O)CC1CO1]<br>7h | 92 |
| 9 | 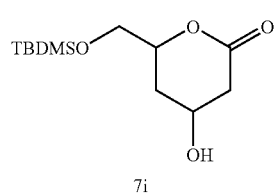 [SMILES: CC(C)(C)[Si](C)(C)OCC1CC(O)CC(=O)O1]<br>6i | (TBDMSO lactone)<br>7i | 52 |

TABLE 2-continued

Synthesis of 3HLs using HCo(CO)₄

R'(OH)(R)CH₂-epoxide + CO (800 psi) →[2 mol % HCo(CO)₄, 60° C., 24 h, 1.0M DME]→ δ-lactone (R', R on ring, OH)

| | epoxide | | | |
|---|---|---|---|---|
| entry | R | R' | δ-lactone | yield[a] (%) |
| 10 | Cl-CH₂- | OH | Cl-CH₂-(δ-lactone with OH) | 81 |
| | 6j | | 7j | |

[a] Yield of isolated product.
[b] 6% β-Lactone formed.
[c] 4% β-Lactone formed.
[d] 5 mol % Catalyst used.

Example 7

Carbonylation of Enantiopure Homoglycidol (R,R)-6b with Retention of Stereochemistry

The ability to control the stereochemical outcome of the carbonylation is of great importance for any synthetic application. To test whether or not this method affords retention of stereochemistry, (R,R)-6b was carbonylated under standard conditions as shown below.

Scheme 2. Carbonylation of enantiopure homoglycidol (R,R)-6B with retention of stereochemistry.

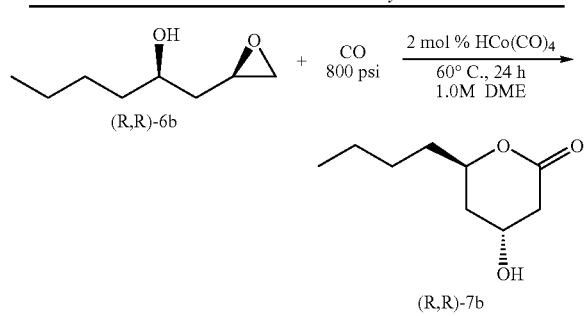

Analysis by ¹H and ¹³C NMR spectroscopy indicated the trans diastereomer was formed exclusively, and optical rotation established the product as the (3R,5R) isomer. Thus, the carbonylation occurs with retention of both stereocenters.

Example 8

Carbonylation of 4-hydroxy-1,2-epoxynonane (6) monitored by in situ IR spectroscopy

The adapted Parr reactor was dried under vacuum overnight and brought into the glove box. A solution of 6 (0.79 g, 5.0 mmol) in 5.0 mL DME was drawn into a 10 mL glass syringe. Another solution containing HCo(CO)₄ (0.1 mmol in 5.0 mL DME) was drawn into a separate glass syringe. The needles from each syringe were inserted through a septum covering the injection port of the reactor. The reactor was removed from the glove box, connected to the ReactIR, and a background spectrum was recorded. Following the background, both the epoxide and catalyst solutions were injected into the reactor, which was then pressured to 800 psi with CO. While IR spectra were recorded every two minutes, the reactor was heated to 60° C. using a heating jacket. The formation of δ-lactone (7) and β-lactone (8) was monitored by the emergence of their carbonyl stretches at 1744 cm⁻¹ and 1827 cm⁻¹, respectively (FIG. S1). The reaction was allowed to proceed until the lactone absorbance was constant, at which time the reactor was cooled and vented. The crude reaction mixture was analyzed by ¹H NMR spectroscopy.

Isomerization of β-Lactone (8) Monitored by In Situ IR Spectroscopy.

A mixture of 7 and 8 was prepared under standard carbonylation conditions using catalyst 1 (see Table 1, entry 1). Catalyst residue was removed by passing the crude reaction mixture though a plug of silica with CH₂Cl₂ and removing solvent in vacuo. The lactone mixture was then dried over activated 4 Å molecular sieves and degassed three times by freeze-pump-thaw cycles. The dried Parr reactor was connected to the React-IR and a background spectrum was acquired. Next, 930 mg (5.0 mmol) of 7/8 in 5 mL DME was added to the reactor which was pressured to 800 psi with CO. The reactor was heated to 60° C. while acquiring a spectrum every minute until the absorbances (CO stretches measured at 1744 cm⁻¹ and 1827 cm⁻¹ for δ-lactone and β-lactone, respectively) of the two lactones remained constant. The reactor was then carefully vented to 50 psi CO and a solution of 0.1 mmol HCo(CO)₄ in 5 mL DME was added via syringe through the injector port. The reactor was then repressured to 800 psi CO and the absorbances of 7 and 8 were monitored by continuing to acquire IR spectra every minute. The profile of the IR spectra is shown in FIG. S2. Since no isomerization of 8 to 7 is observed under the reaction conditions, 8 is eliminated as a possible intermediate in the carbonylation of 6 to 7.

REFERENCES (1) Gogoi, S.; Barua, N. C.; Kalita, B. *Tetrahedron Lett.* 2004, 45, 5577-5579.
(2) Le Sann, C.; Muñoz, D. M.; Saunders, N.; Simpson, T. J.; Smith, D. I.; Soulas, F.; Watts, P.; Willis, C. L. *Org. Biomol. Chem.* 2005, 3, 1719-1728.
(3) Aprile, C.; Gruttadauria, M.; Amato, M. E.; D'Anna, F.; Lo Meo, P. Riela, S.; Noto, R. *Tetrahedron,* 2003, 59, 2241-2251.
(4) Molander, G. A.; Etter, J. B.; Harring, L. S.; Thorel, P.- J. *J. Am. Chem. Soc.* 1991, 113, 8036-8045.
(5) MacKeith, R. A.; McCague, R.; Olivo, H. F.; Roberts, S. M.; Taylor, S. J. C.; Xiong, H. *Bioorg. Med. Chem.* 1994, 2, 387-394.
(6) Greenberg, W. A.; Varvak, A.; Hanson, S. R.; Wong, K.; Huang, H.; Chen, P.; Burk, M. *Proc. Natl. Acad. Sci. U.S.A.* 2004, 101, 5788-5793.
(7) Getzler, Y. D. Y. L.; Kundnani, V.; Lobkovsky, E. B.; Coates, G. W. *J. Am. Chem. Soc.* 2004, 126, 6842-6843.
(8) Kramer, J. W.; Lobkovsky, E. B.; Coates, G. W. *Org. Lett.* 2006, 8, 3709-3712.
(9) Getzler, Y. D. Y. L.; Mahadevan, V.; Lobkovsky, E. B.; Coates, G. W. *J. Am. Chem. Soc.* 2002, 124, 1174-1175.
(10) Schmidt, J. A. R.; Mahadevan, V.; Getzler, Y. D. Y. L.; Coates, G. W. *Org. Lett.* 2004, 6, 373-376.
(11) Rowley, J. M.; Lobkovsky, E. B.; Coates, G. W. *J. Am. Chem. Soc.* 2007, 129, 4948-4960.
(12) Mahadevan, V.; Getzler, Y. D. Y. L.; Coates, G. W. *Angew. Chem. Int. Ed.* 2002, 41, 2781-2784.
(13) Harrod, J. F.; Chalk, A. J. *J. Am. Chem. Soc.* 1965, 87, 1133-1135.
(14) Ishikawa, M.; Amaike, M.; Itoh, M.; Warita, Y.; Kitahara, T. *Biosci. Biotechnol. Biochem.* 2003, 67, 2210-2214.
(15) Brown, H. C.; Lynch, G. J. *J. Org. Chem.* 1981, 46, 930-939.
(16) Banerjee, B.; Roy, S. C. *Eur. J. Org. Chem.* 2006, 489-497.
(17) Murray, R. W.; Gu, H. *J. Phys. Org. Chem.* 1996, 9, 751-758.
(18) Bats, J. P.; Moulines, J.; Leclercq, D. *Tetrahedron* 1982, 38, 2139-2146.
(19) Palombi, L.; Bonadies, F.; Scettri, A. *Tetrahedron* 1997, 53, 11369-11376.
(20) Schaus, S. E.; Brandes, B. D.; Larrow, J. F.; Tokunaga, M.; Hansen, K. B.; Gould, A. E.; Furrow, M. E.; Jacobsen, E. N. *J. Am. Chem. Soc.* 2002, 124, 1307-1315.
(21) Byrne, C. M.; Church, T. L.; Kramer, J. W.; Lobkovsky, E. B.; Coates, G. W. *Manuscript in Preparation*.
(23) The R,R diastereomer of 6-pentyl-4-hydroxy-δ-lactone has been reported: $[\alpha]^{23}_D$+32.1 (c=0.92, CHCl$_3$). Romeyke, Y.; Keller, M.; Kluge, H.; Grabley, S.; Hammann, P. *Tetrahedron* 1991, 47, 3335-3339. The optical rotation of (R,R)-7b is in line with the literature report for the analogous compound in both magnitude and direction of rotation.

Other Embodiments

Other embodiments of the invention will be apparent to those skilled in the art from a consideration of the specification or practice of the invention disclosed herein. It is intended that the specification and Examples be considered as exemplary only, with the true scope of the invention being indicated by the following claims. The contents of any reference that is referred to herein are hereby incorporated by reference in their entirety.

We claim:
1. A method comprising the steps of:
reacting an epoxide of formula:

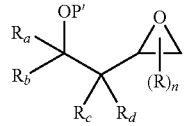

wherein:
n is an integer between 0 and 3, inclusive;
$R_a$ and $R_b$ are each independently hydrogen; halogen; $C_1$ to $C_{20}$ alkyl; $C_2$ to $C_{20}$ alkenyl; $C_2$ to $C_{20}$ alkynyl; up to a $C_{16}$ carbocycle; up to a $C_{16}$ heterocycle; —C($R^{13}$)$_z$H$_{(3-z)}$; or a polymer chain; or
$R_a$ and $R_b$ are taken together with intervening atoms to form one or more optionally substituted rings optionally containing one or more heteroatoms, and either of $R_a$ or $R_b$ may optionally be further substituted with one or more X groups;
$R_c$, $R_d$, and each R group are hydrogen;
P' is hydrogen;
each occurrence of X is independently halogen; a phosphorus-containing moiety, —OR$^{10}$; —OC(O)R$^{13}$; —OC(O)OR$^{13}$; —OC(O)NR$^{11}$R$^{12}$; —CN; —CNO; —C(O)R$^{13}$; —C(O)OR$^{13}$; —C(O)NR$^{11}$R$^{12}$; —C(R$^{13}$))$_z$H$_{(3-z)}$; —NR$^{11}$C(O)R$^{10}$; —NR$^{11}$C(O)OR$^{10}$; —NCO; —NR$^{12}$SO$_2$R$^{13}$; —S(O)$_x$R$^{13}$; —S(O)$_2$NR$^{11}$R$^{12}$; —NO$_2$; —N$_3$; —(CH$_2$)$_k$R$^{14}$; —(CH$_2$)$_k$—Z—R$^{14}$; and —(CH$_2$)$_k$—Z—(CH$_2$)$_m$—R$^{14}$;
$R^{10}$ at each occurrence can be independently selected from the group consisting of: hydrogen; —C(R$^{13}$)$_z$H$_{(3-z)}$; $C_1$ to $C_{12}$ alkyl; $C_2$ to $C_{12}$ alkenyl; $C_2$ to $C_{12}$ alkynyl; up to a $C_{12}$ carbocycle; up to a $C_{12}$ heterocycle; —S(O)$_2$R$^{13}$; —Si(R$^{15}$)$_3$; and a hydroxyl protecting group;
$R^{11}$ and $R^{12}$ at each occurrence can be independently selected from the group consisting of: hydrogen; $C_1$ to $C_{12}$ alkyl; $C_2$ to $C_{12}$ alkenyl; $C_2$ to $C_{12}$ alkynyl; and —C(R$^{13}$)$_z$H$_{(3-z)}$;
$R^{11}$ and $R^{12}$, when both present, can optionally be taken together with the atom to which they are attached to form an optionally substituted 3- to 10-membered ring, optionally containing one or more additional heteroatoms;
$R^{13}$ at each occurrence can be independently selected from the group consisting of: hydrogen; halogen; $C_1$ to $C_{12}$ alkyl; $C_2$ to $C_{12}$ alkenyl; $C_2$ to $C_{12}$ alkynyl; up to a $C_{12}$ carbocycle; or up to a $C_{12}$ heterocycle;
$R^{14}$ at each occurrence can be independently selected from the group consisting of halogen; —OR$^{10}$; —OC(O)R$^{13}$; —OC(O)OR$^{13}$; —OC(O)NR$^{11}$R$^{12}$; —CN; —CNO; —C(R$^{13}$)$_z$H$_{(3-z)}$; —C(O)R$^{13}$; —C(O)OR$^{13}$; —C(O)NR$^{11}$R$^{12}$; —NR$^{11}$C(O)R$^{13}$; —NR$^{11}$C(O)OR$^{10}$; —NR$^{11}$SO$_2$R$^{13}$; —NCO; —N$_3$; —NO$_2$; —S(O)$_x$R$^{13}$; —SO$_2$NR$^{11}$R$^{12}$; up to a $C_{12}$ heterocycle; and up to a $C_{12}$ carbocycle;
$R^{15}$ at each occurrence can be independently selected from the group consisting of: $C_1$ to $C_6$ alkyl; $C_2$ to $C_6$ alkenyl; $C_2$ to $C_6$ alkynyl; and up to $C_{12}$ substituted or unsubstituted carbocycle;
Z is a divalent linker and can be selected from the group consisting of: —(CH=CH)$_a$—; —(CH≡CH)$_a$—; —C(O)—; —C(=NOR$^{11}$)—; —C(=NNR$^{11}$R$^{12}$)—; —O—; —N(R$^{11}$)—; —N(C(O)R$^{13}$)—; —S(O)$_x$; a polyether; and a polyamine;
a can be 1, 2, 3, or 4;

k can be an integer from 1 to 8 inclusive;
m can be an integer from 1 to 8 inclusive;
x can be 0, 1, or 2; and
z can be 1, 2, or 3;
with carbon monoxide (CO) in the presence of a catalytically effective amount of a catalyst of the formula:

$$[\text{Lewis acid}]^{u+}\{[QT(CO)_v]^{s-}\}^t \qquad \text{II}$$

wherein:
Q is any ligand or set of ligands and need not be present;
T is a metal selected from group 7, 8, or 9 of the periodic table;
s is an integer from 1 to 4 inclusive;
t is a number such that t multiplied by s equals u;
u is an integer from 1 to 6 inclusive;
v is an integer from 1 to 9 inclusive; and
the Lewis acid is H+ or is of formula $[M(L)_b]^{c+}$, wherein
M is a transition metal or group 13 or 14 metal;
L is a ligand and need not be present;
b is an integer from 1 to 6, inclusive; and
c is 1, 2, or 3;
to produce a compound of the formula:

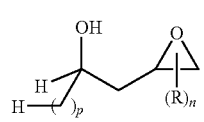

2. The method of claim 1, wherein the epoxide is of the formula:

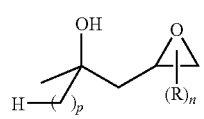

wherein p is an integer between 1 and 4, inclusive.

3. The method of claim 1, wherein the epoxide is of the formula:

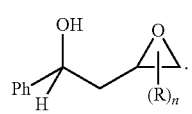

wherein p is an integer between 1 and 4, inclusive.

4. The method of claim 1, wherein the epoxide is of the formula:

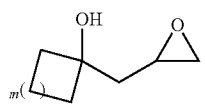

5. The method of claim 1, wherein the epoxide is of the formula:

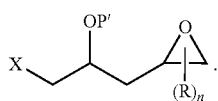

wherein m is an integer between 0 and 10, inclusive.

6. The method of claim 1, wherein the epoxide is of the formula:

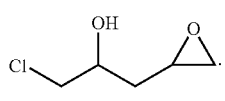

7. The method of claim 6, wherein X is a halogen.

8. The method of claim 6, wherein X is chlorine.

9. The method of claim 1, wherein the epoxide is of the formula:

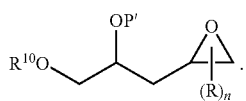

10. The method of claim 1, wherein the epoxide is of the formula:

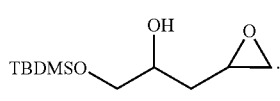

11. The method of claim 10, wherein $R^{10}$ is a suitable protecting group or hydrogen.

12. The method of claim 11, wherein $R^{10}$ is a silyl protecting group.

13. The method of claim 12, wherein $R^{10}$ is tert-butyldimethylsilyl.

14. The method of claim 1, wherein the epoxide is of the formula:

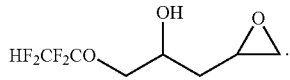

15. The method of claim 1, wherein the epoxide is of the formula:

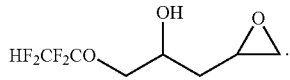

16. The method of claim 1, wherein the epoxide is of the formula:

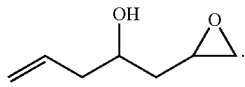

17. The method of claim 1, wherein the epoxide is of the formula:

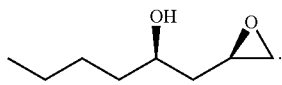

18. The method of claim 1, wherein T is cobalt.
19. The method of claim 1, wherein Q is absent.
20. The method of claim 1, wherein v is 4.
21. The method of claim 1, wherein the Lewis acid is $H^+$.
22. The method of claim 1, wherein the carbonylation catalyst is $HCo(CO)_4$.
23. The method of claim 1, wherein the Lewis acid is of formula IIIa:

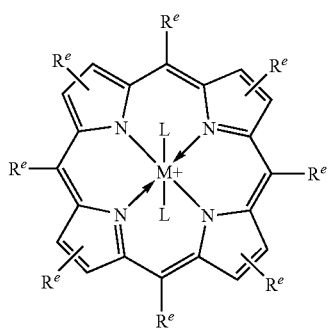

wherein:
$R^e$ at each occurrence is independently selected from the group consisting of: hydrogen; $C_1$-$C_{12}$ alkyl; $C_2$-$C_{12}$ alkenyl; $C_2$-$C_{12}$ alkynyl; aryl; heteroaryl; halogen; —$OR^{10}$; —$OC(O)R^{13}$; —$OC(O)OR^{13}$; —$OC(O)NR^{11}R^{12}$; —$CN$; —$CNO$; —$C(O)R^{13}$; —$C(R^{13})_zH_{(3-z)}$; —$C(O)OR^{13}$; —$C(O)NR^{11}R^{12}$; —$NR^{11}R^{12}$; —$NR^{11}C(O)R^{10}$; —$NR^{11}C(O)OR^{13}$; —$NR^{11}SO_2R^{13}$; —$NCO$; —$N_3$; —$NO_2$; —$S(O)_xR^{13}$; —$SO_2NR^{11}R^{12}$; —$C(R^{13})_zH_{(3-z)}$; —$(CH_2)_kR^{14}$; —$(CH_2)_k$—Z—$R^{16}$—; and —$(CH_2)_k$—Z—$(CH_2)_m$—$R^{14}$, where two or more $R^e$ groups may optionally be taken together to form an optionally substituted ring; and
wherein M, L, $R^{10}$, $R^{11}$, $R^{12}$, $R^{13}$, $R^{14}$, $R^{16}$, Z, k, m, x, and z are as defined in claim 1.

24. The method of claim 23, wherein M is Al.
25. The method of claim 23, wherein the Lewis acid is of formula IIIa(ii):

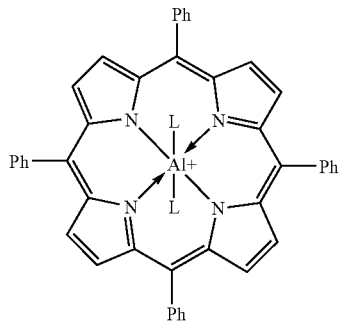

wherein -Ph represents an optionally substituted phenyl group and L is as defined in claim 1.

26. The method of claim 23, wherein the carbonylation catalyst is of formula IIa(i):

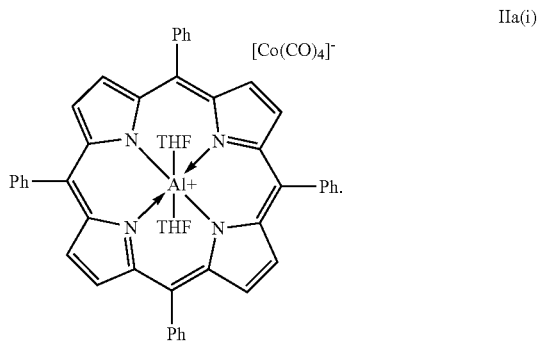

27. The method of claim 1, wherein the Lewis acid is of formula IIIb:

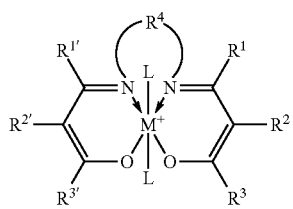

wherein:
$R^1$ and $R^{1'}$ are independently selected from the group consisting of: hydrogen; $C_1$ to $C_{12}$ alkyl; $C_2$ to $C_{12}$ alkenyl; $C_2$ to $C_{12}$ alkynyl; —$C(R^{13})_zH_{(3-z)}$; —$(CH_2)_kR^{14}$; and —$(CH_2)_k$—Z—$R^{14}$;
$R^2$, $R^{2'}$, $R^3$, and $R^{3'}$ are independently selected from the group consisting of: (i) $C_1$-$C_{12}$ alkyl; (ii) $C_2$-$C_{12}$ alkenyl; (iii) $C_2$-$C_{12}$ alkynyl; (iv) up to a $C_{12}$ carbocycle; (v) up to a $C_{12}$ heterocycle; (vi) —$(CH_2)_kR^{14}$; (vii) $R^{20}$; and (viii) —$C(R^{13})_zH_{(3-z)}$,
wherein each of (i) through (v) may optionally be further substituted with one or more $R^{20}$ groups; and where $R^2$ and $R^3$, and $R^{2'}$ and $R^{3'}$ may optionally be taken together with the carbon atoms to which they are attached to form one or more rings which may in turn be substituted with one or more $R^{20}$ groups;

$R^4$ is selected from the group consisting of:

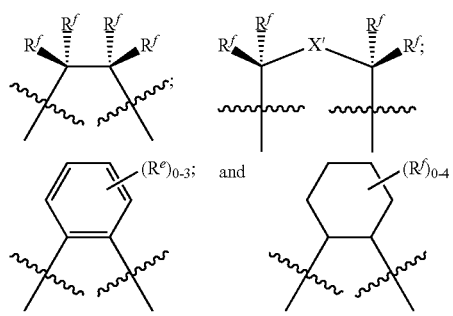

wherein X' is a divalent linker selected from the group consisting of: —N($R^{11}$)—; —O—; —S(O)$_x$—; —(CH$_2$)$_k$—; —C(O)—; —C(=NOR$^{10}$)—; —C(R$^f$)$_2$—; a polyether; a $C_3$ to $C_8$ substituted or unsubstituted carbocycle; and a $C_1$ to $C_8$ substituted or unsubstituted heterocycle;

$R^e$ is as defined above;

$R^f$ at each occurrence is independently selected from the group consisting of: (a) $C_1$-$C_{12}$ alkyl; (b) $C_2$-$C_{12}$ alkenyl, (c) $C_2$-$C_{12}$ alkynyl; (e) up to a $C_{12}$ carbocycle, (f) up to a $C_{12}$ heterocycle; (g) $R^{20}$; and (h) —C($R^{13}$)$_z$H$_{(3-z)}$; or wherein:

two or more $R^f$ groups may be taken together with the carbon atoms to which they are attached to form one or more rings; or wherein when two $R^f$ groups are attached to the same carbon atom, they may be taken together to form a moiety selected from the group consisting of: a 3- to 8-membered spirocyclic ring; a carbonyl (C=O), an oxime (C=NOR$^{10}$); a hydrazone (C=NNR$^{11}$R$^{12}$); an imine (C=NR$^{11}$); and an alkenyl group (C=CR$^{11}$R$^{12}$);

$R^{20}$ at each occurrence is independently selected from the group consisting of: hydrogen; halogen; —OR$^{10}$; —OC(O)R$^{13}$; —OC(O)OR$^{13}$; —OC(O)NR$^{11}$R$^{12}$; —CN; —CNO; —C(O)R$^{13}$; —C(O)OR$^{13}$; —C(O)NR$^{11}$R$^{12}$; —C(R$^{13}$)$_z$H$_{(3-z)}$; —NR$^{11}$R$^{12}$; —NR$^{11}$C(O)R$^{10}$; —NR$^{11}$C(O)OR$^{10}$; —NCO; —NR$^{12}$SO$_2$R$^{13}$; —S(O)$_x$R$^{13}$; —S(O)$_2$NR$^{11}$R$^{12}$; —NO$_2$; —N$_3$; —(CH$_2$)$_k$R$^{14}$; —(CH$_2$)$_k$—Z—R$^{16}$; and —(CH$_2$)$_k$—Z—(CH$_2$)$_m$—R$^{14}$; and L, M, $R^{10}$, $R^{11}$, $R^{12}$, $R^{13}$, $R^{14}$, $R^{16}$, Z, k, m, x, and z are as defined in claim 1.

28. The method of claim 27, wherein M is Al.

29. The method of claim 27, wherein the Lewis acid is of formula IIIb(i):

IIIb(i)

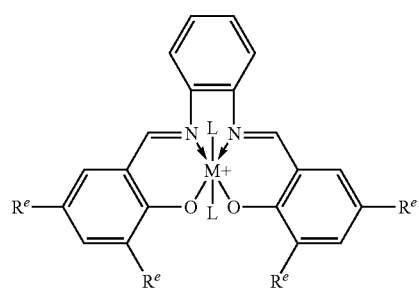

wherein M is Al and L is as defined in claim 1.

30. The method of claim 27, wherein the carbonylation catalyst is of formula IIb(ii):

IIb(ii)

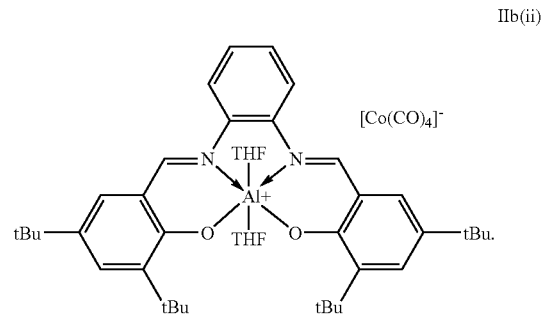

31. The method of claim 1, wherein the Lewis acid is of formula IIIc:

IIIc

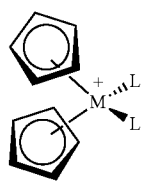

wherein M and L are as defined in claim 1.

32. The method of claim 31, wherein M is Ti.

33. The method of claim 31, wherein the carbonylation catalyst is of formula IIc(i):

IIc(i)

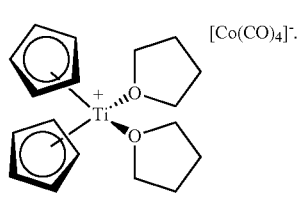

34. The method of claim 1, wherein carbonylation proceeds with retention of stereochemistry.

35. A method comprising steps of:

reacting an epoxide of formula S-Ia':

S-Ia'

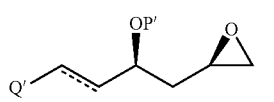

wherein:

═══ is a single bond;

P' is hydrogen;

Q' is selected from the group consisting of: hydrogen; halogen; (a) $C_1$ to $C_{20}$ alkyl; (b) $C_2$ to $C_{20}$ alkenyl; (c) $C_2$ to $C_{20}$ alkynyl; (d) up to a $C_{16}$ carbocycle; (e) up to a $C_{16}$ heterocycle; and (f) —C($R^{13}$)$_z$H$_{(3-z)}$; or Q' is a core of a statin molecule;

with carbon monoxide (CO) in the presence of a catalytically effective amount of a catalyst of the formula:

[Lewis acid]$^{u+}$\{[QT(CO)$_v$]$^{s-}$\}$^t$    II wherein:

Q is any ligand or set of ligands and need not be present;

T is a metal selected from group 7, 8, or 9 of the periodic table;

s is an integer from 1 to 4 inclusive;

t is a number such that t multiplied by s equals u;

u is an integer from 1 to 6 inclusive;

v is an integer from 1 to 9 inclusive; and the Lewis acid is H+ or is of formula $[M(L)_b]^{c+}$, wherein M is a transition metal or group 13 or 14 metal;

L is a ligand and need not be present;

b is an integer from 1 to 6, inclusive; and c is 1, 2, or 3;

to produce a compound of the formula S-I′:

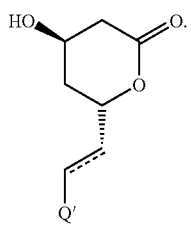

S-I′

36. The method of claim 35, wherein the statin molecule is selected from the group consisting of: atorvastatin, lovastatin, mevastatin, pravastatin, and simvastatin.

37. The method of claim 36, wherein the statin molecule is atorvastatin.

38. The method of claim 35, wherein the

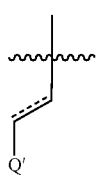

moiety is selected from the group consisting of:

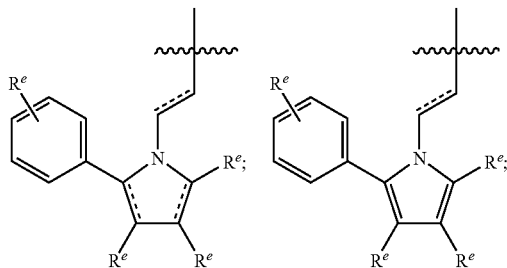

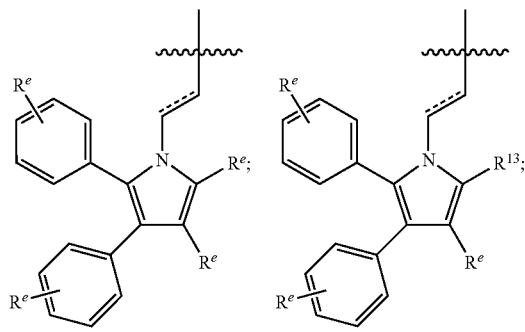

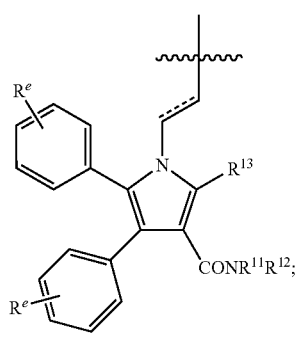

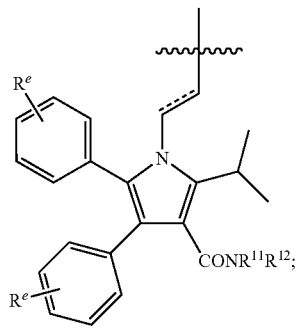

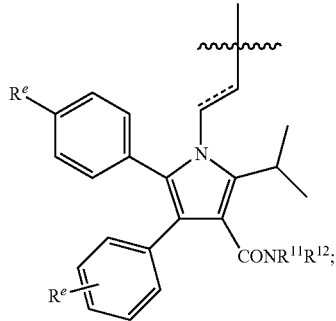

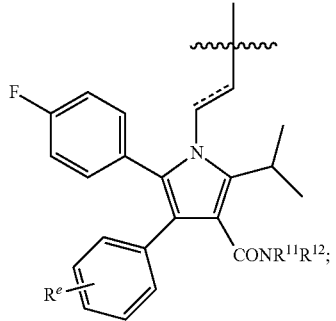

-continued

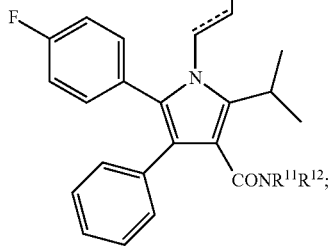

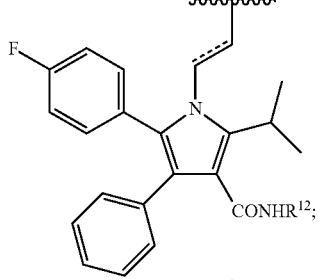

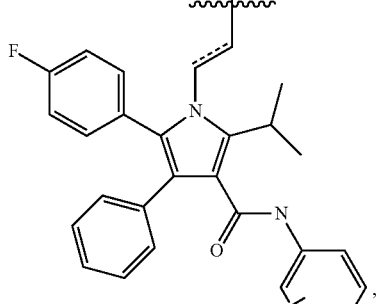

wherein $R^e$ at each occurrence is independently selected from the group consisting of: hydrogen; $C_1$-$C_{12}$ alkyl; $C_2$-$C_{12}$ alkenyl; $C_2$-$C_{12}$ alkynyl; aryl; heteroaryl; halogen; —$OR^{10}$; —$OC(O)R^{13}$; —$OC(O)OR^{13}$; —$OC(O)NR^{11}R^{12}$; —CN; —CNO; —$C(O)R^{13}$; —$C(R^{13})_zH_{(3-z)}$; —$C(O)OR^{13}$; —$C(O)NR^{11}R^{12}$; —$NR^{11}R^{12}$; —$NR^{11}C(O)R^{10}$; —$NR^{11}C(O)OR^{13}$; —$NR^{11}SO_2R^{13}$; —NCO; —$N_3$; —$NO_2$; —$S(O)_xR^{13}$; —$SO_2NR^{11}R^{12}$; —$C(R^{13})_zH_{(3-z)}$; —$(CH_2)_kR^{14}$; —$(CH_2)_k$—Z—$R^{16}$—; and —$(CH_2)_k$—Z—$(CH_2)_m$—$R^{14}$, where two or more $R^e$ groups may optionally be taken together to form an optionally substituted ring; and $R^{10}$, $R^{11}$, $R^{12}$, $R^{13}$, $R^{14}$, $R^{16}$, Z, k, m, x, and z are as defined in claim 1.

39. The method of claim 35, wherein the moiety is selected from the group consisting of:

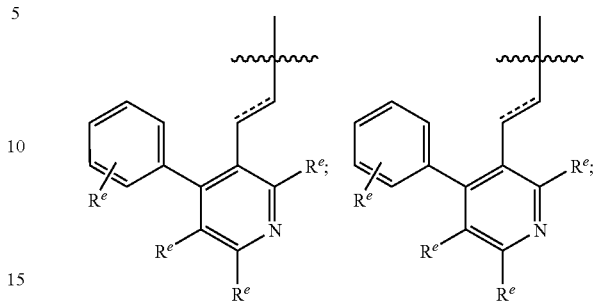

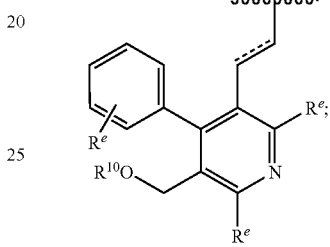

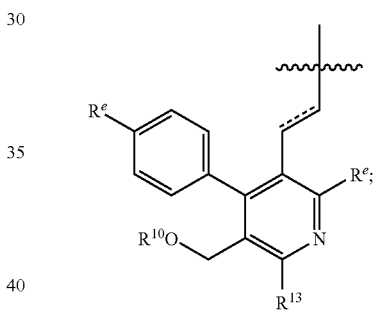

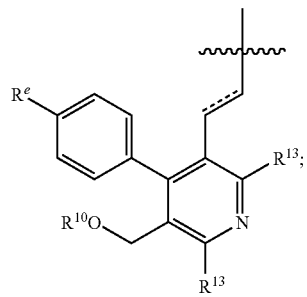

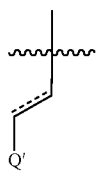

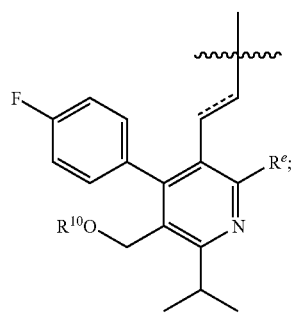

-continued

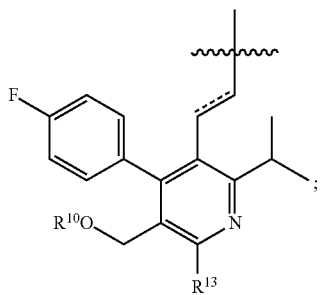

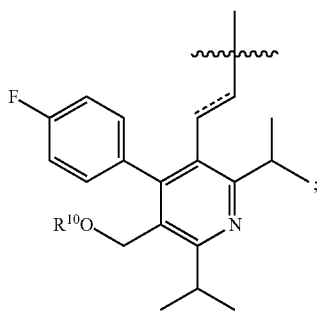

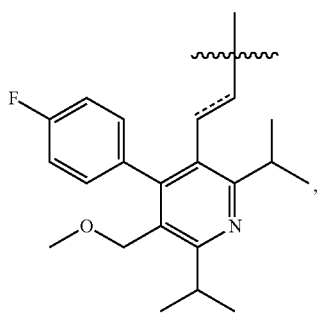

wherein $R^e$ at each occurrence is independently selected from the group consisting of: hydrogen; $C_1$-$C_{12}$ alkyl; $C_2$-$C_{12}$ alkenyl; $C_2$-$C_{12}$ alkynyl; aryl; heteroaryl; halogen; —$OR^{10}$; —$OC(O)R^{13}$; —$OC(O)OR^{13}$; —$OC(O)NR^{11}R^{12}$; —CN; —CNO; —$C(O)R^{13}$; —$C(R^{13})_zH_{(3-z)}$; —$C(O)OR^{13}$; —$C(O)NR^{11}R^{12}$; —$NR^{11}R^{12}$; —$NR^{11}C(O)R^{10}$; —$NR^{11}C(O)OR^{13}$; —$NR^{11}SO_2R^{13}$; —NCO; —$N_3$; —$NO_2$; —$S(O)_xR^{13}$; —$SO_2NR^{11}R^{12}$; —$C(R^{13})_zH_{(3-z)}$; —$(CH_2)_kR^{14}$; —$(CH_2)_k$—Z—$R^{16}$—; and —$(CH_2)_k$—Z—$(CH_2)_m$—$R^{14}$, where two or more $R^e$ groups may optionally be taken together to form an optionally substituted ring; and $R^{10}$, $R^{11}$, $R^{12}$, $R^{13}$, $R^{14}$, $R^{16}$, Z, k, m, x, and z are as defined in claim 1.

40. The method of claim 35, wherein the

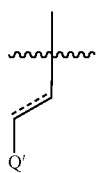

moiety is selected from the group consisting of:

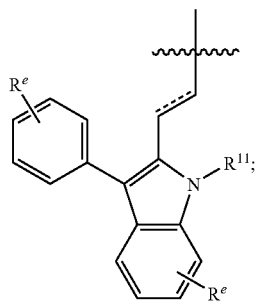

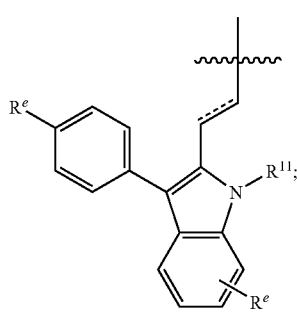

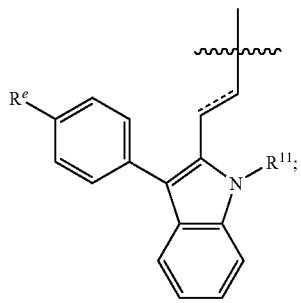

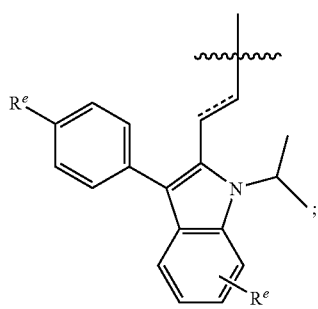

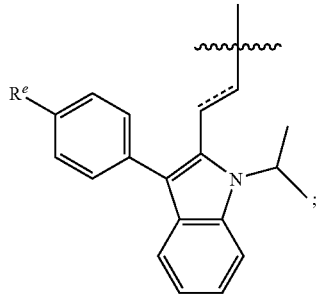

-continued

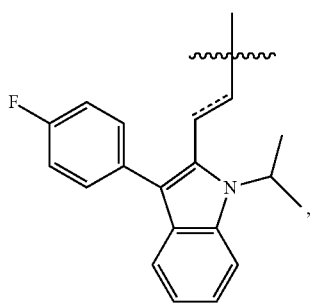

wherein $R^e$ at each occurrence is independently selected from the group consisting of: hydrogen; $C_1$-$C_{12}$ alkyl; $C_2$-$C_{12}$ alkenyl; $C_2$-$C_{12}$ alkynyl; aryl; heteroaryl; halogen; —$OR^{10}$; —$OC(O)R^{13}$; —$OC(O)OR^{13}$; —$OC(O)NR^{11}R^{12}$; —$CN$; —$CNO$; —$C(O)R^{13}$; —$C(R^{13})_zH_{(3-z)}$; —$C(O)OR^{13}$; —$C(O)NR^{11}R^{12}$; —$NR^{11}R^{12}$; —$NR^{11}C(O)R^{10}$; —$NR^{11}C(O)OR^{13}$; —$NR^{11}SO_2R^{13}$; —$NCO$; —$N_3$; —$NO_2$; —$S(O)_xR^{13}$; —$SO_2NR^{11}R^{12}$; —$C(R^{13})_zH_{(3-z)}$; —$(CH_2)_kR^{14}$; —$(CH_2)_k$—$Z$—$R^{16}$—; and —$(CH_2)_k$—$Z$—$(CH_2)_m$—$R^{14}$, where two or more $R^e$ groups may optionally be taken together to form an optionally substituted ring; and $R^{10}$, $R^{11}$, $R^{12}$, $R^{13}$, $R^{14}$, $R^{16}$, $Z$, k, m, x, and z are as defined in claim 1.

41. The method of claim 36, wherein the statin molecule is lovastatin.

42. The method of claim 35, wherein the

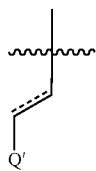

moiety is selected from the group consisting of:

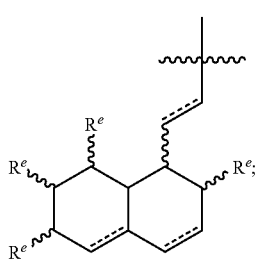

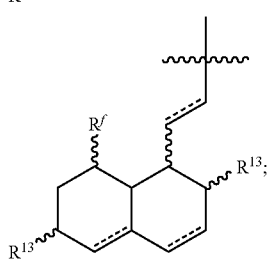

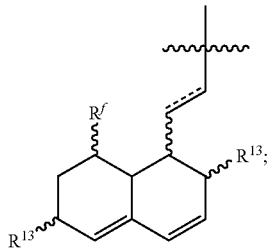

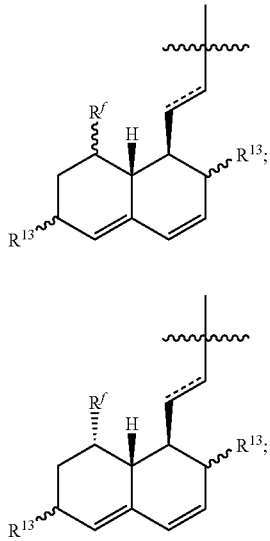

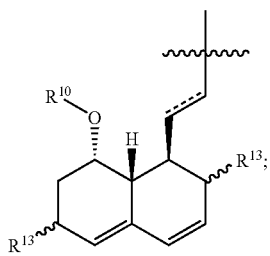

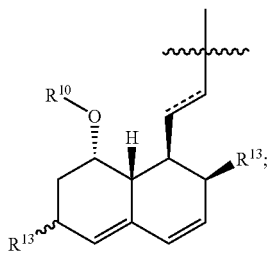

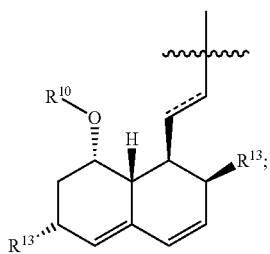

-continued

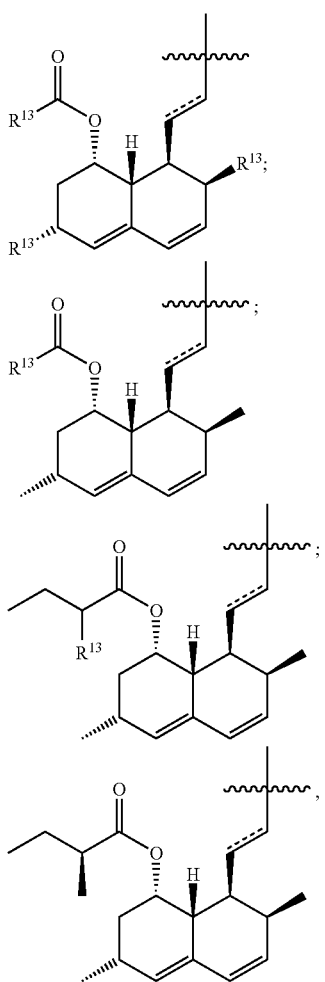

wherein $R^e$ at each occurrence is independently selected from the group consisting of: hydrogen; $C_1$-$C_{12}$ alkyl; $C_2$-$C_{12}$ alkenyl; $C_2$-$C_{12}$ alkynyl; aryl; heteroaryl; halogen; —$OR^{10}$; —$OC(O)R^{13}$; —$OC(O)OR^{13}$; —$OC(O)NR^{11}R^{12}$; —CN; —CNO; —$C(O)R^{13}$; —$C(R^{13})_zH_{(3-z)}$; —$C(O)OR^{13}$; —$C(O)NR^{11}R^{12}$; —$NR^{11}R^{12}$; —$NR^{11}C(O)R^{10}$; —$NR^{11}C(O)OR^{13}$; —$NR^{11}SO_2R^{13}$; —NCO; —$N_3$; —$NO_2$; —$S(O)_xR^{13}$; —$SO_2NR^{11}R^{12}$; —$C(R^{13})_zH_{(3-z)}$; —$(CH_2)_kR^{14}$; —$(CH_2)_k$—Z—$R^{16}$—; and —$(CH_2)_k$—Z—$(CH_2)_m$—$R^{14}$, where two or more $R^e$ groups may optionally be taken together to form an optionally substituted ring; and
$R^{10}$, $R^{11}$, $R^{12}$, $R^{13}$, $R^{14}$, $R^{16}$, Z, k, m, x, and z are as defined in claim 1.

43. The method of claim 36, wherein the statin molecule is mevastatin.

44. The method of claim 35, wherein the

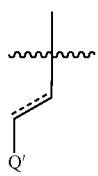

moiety is selected from the group consisting of:

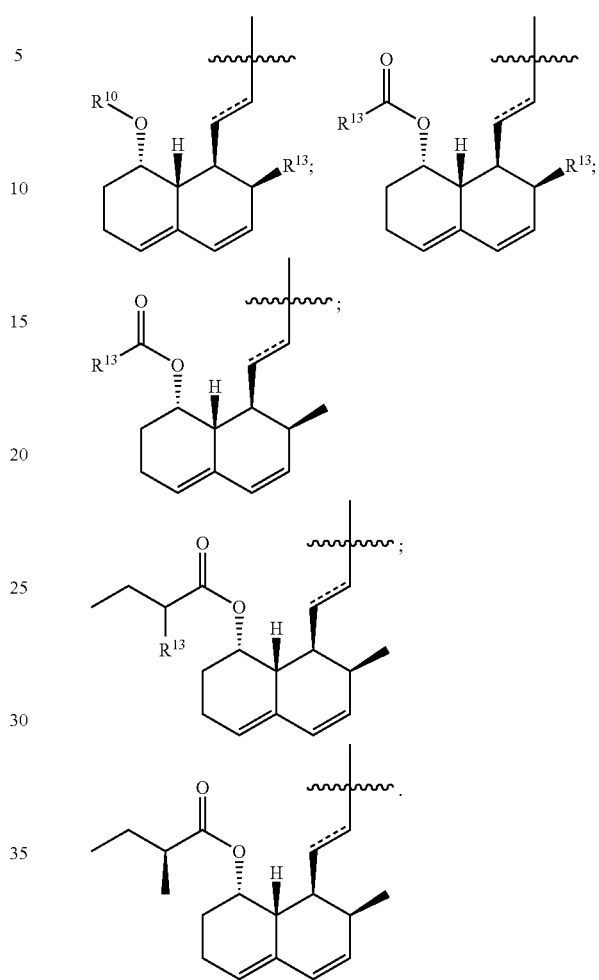

45. The method of claim 35, wherein the

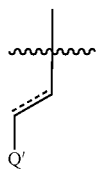

moiety is selected from the group consisting of:

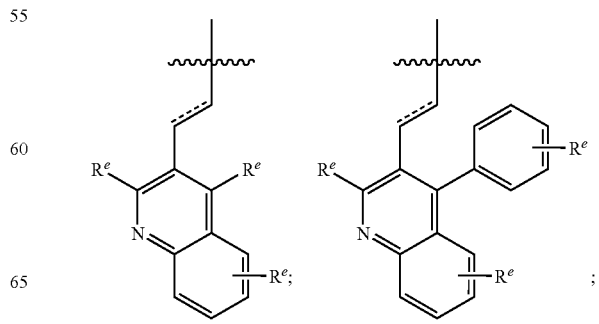

-continued

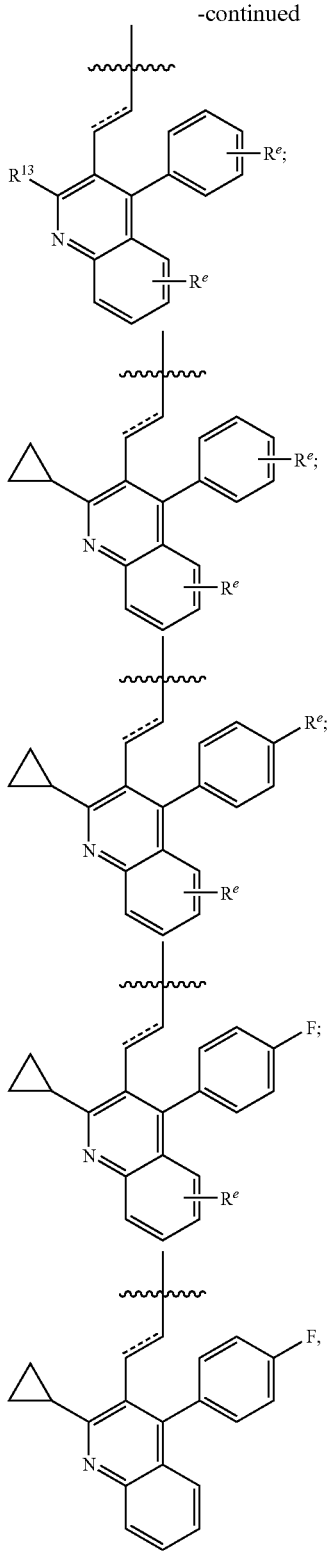

wherein $R^e$ at each occurrence is independently selected from the group consisting of: hydrogen; $C_1$-$C_{12}$ alkyl; $C_2$-$C_{12}$ alkenyl; $C_2$-$C_{12}$ alkynyl; aryl; heteroaryl; halogen; —$OR^{10}$; —$OC(O)R^{13}$; —$OC(O)OR^{13}$; —$OC(O)NR^{11}R^{12}$; —CN; —CNO; —$C(O)R^{13}$; —$C(R^{13})_zH_{(3-z)}$; —$C(O)OR^{13}$; —$C(O)NR^{11}R^{12}$; —$NR^{11}R^{12}$; —$NR^{11}C(O)R^{10}$; —$NR^{11}C(O)OR^{13}$; —$NR^{11}SO_2R^{13}$; —NCO; —$N_3$; —$NO_2$; —$S(O)_xR^{13}$; —$SO_2NR^{11}R^{12}$; —$C(R^{13})_zH_{(3-z)}$; —$(CH_2)_kR^{14}$; —$(CH_2)_k$—Z—$R^{16}$—; and —$(CH_2)_k$—Z—$(CH_2)_m$—$R^{14}$, where two or more $R^e$ groups may optionally be taken together to form an optionally substituted ring; and $R^{10}$, $R^{11}$, $R^{12}$, $R^{13}$, $R^{14}$, $R^{16}$, Z, k, m, x, and z are as defined in claim 1.

46. The method of claim 36, wherein the statin molecule is pravastatin.

47. The method of claim 35, wherein the

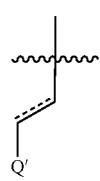

moiety is selected from the group consisting of:

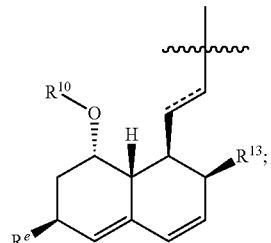

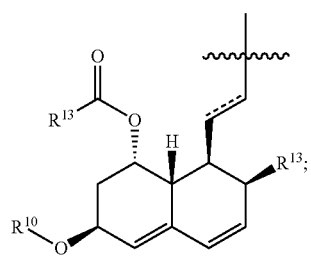

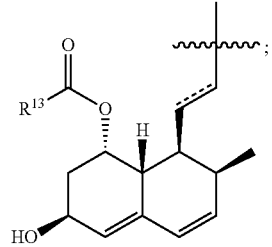

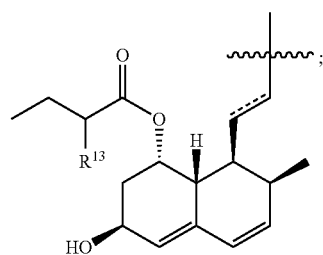

-continued

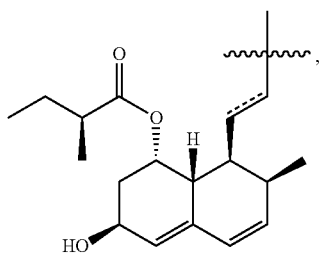

wherein $R^e$ at each occurrence is independently selected from the group consisting of: hydrogen;

$C_1$-$C_{12}$ alkyl; $C_2$-$C_{12}$ alkenyl; $C_2$-$C_{12}$ alkynyl; aryl; heteroaryl; halogen; —$OR^{10}$; —$OC(O)R^{13}$; —$OC(O)OR^{13}$; —$OC(O)NR^{11}R^{12}$; —CN; —CNO; —$C(O)R^{13}$; —$C(R^{13})_zH_{(3-z)}$; —$C(O)OR^{13}$; —$C(O)NR^{11}R^{12}$; —$NR^{11}R^{12}$; —$NR^{11}C(O)R^{10}$; —$NR^{11}C(O)OR^{13}$; —$NR^{11}SO_2R^{13}$; —NCO; —$N_3$; —$NO_2$; —$S(O)_xR^{13}$; —$SO_2NR^{11}R^{12}$; —$C(R^{13})_zH_{(3-z)}$; —$(CH_2)_kR^{14}$; —$(CH_2)_k$—Z—$R^{16}$—; and —$(CH_2)_k$—Z—$(CH_2)_m$—$R^{14}$, where two or more $R^e$ groups may optionally be taken together to form an optionally substituted ring; and $R^{10}$, $R^{11}$, $R^{12}$, $R^{13}$, $R^{14}$, $R^{16}$, Z, k, m, x, and z are as defined in claim 1.

48. The method of claim 35, wherein the

moiety is selected from the group consisting of:

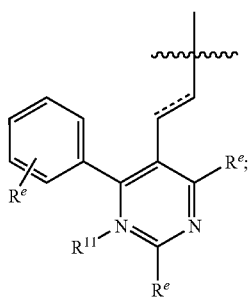

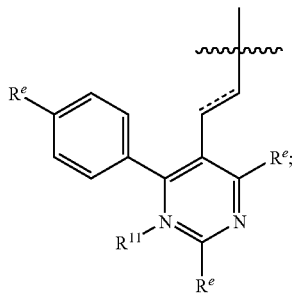

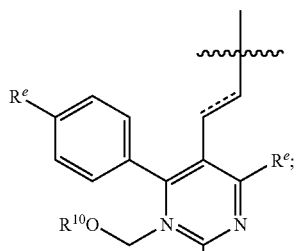

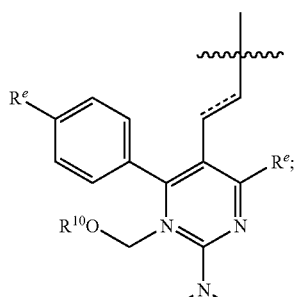

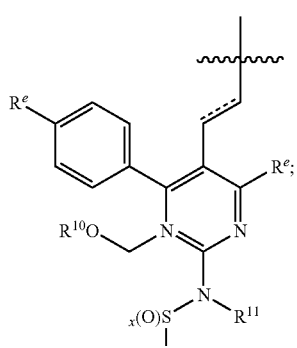

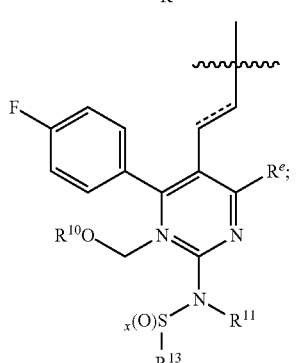

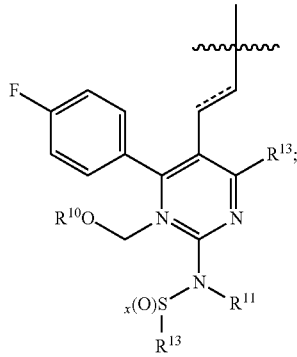

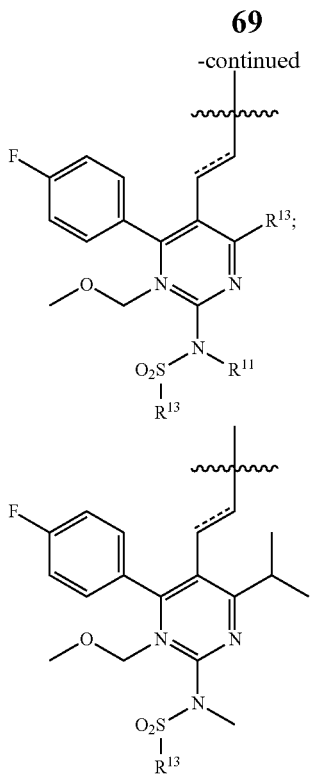

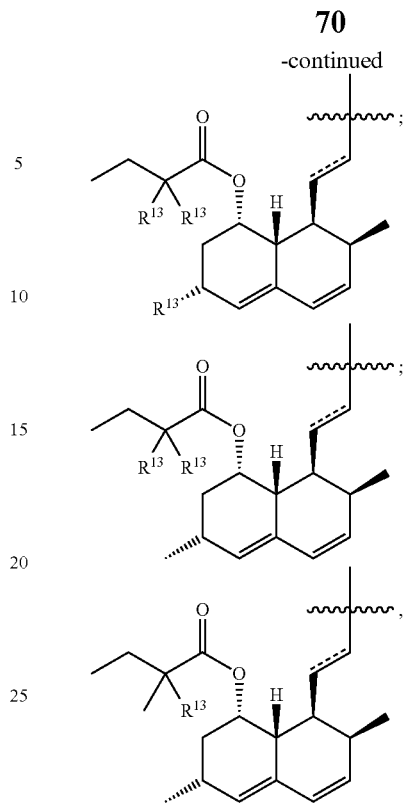

wherein R^e at each occurrence is independently selected from the group consisting of: hydrogen; $C_1$-$C_{12}$ alkyl; $C_2$-$C_{12}$ alkenyl; $C_2$-$C_{12}$ alkynyl; aryl; heteroaryl; halogen; —$OR^{10}$; —$OC(O)R^{13}$; —$OC(O)OR^{13}$; —$OC(O)NR^{11}R^{12}$; —CN; —CNO; —$C(O)R^{13}$; —$C(R^{13})_zH_{(3-z)}$; —$C(O)OR^{13}$; —$C(O)NR^{11}R^{12}$; —$NR^{11}R^{12}$; —$NR^{11}C(O)R^{10}$; —$NR^{11}C(O)OR^{13}$; —$NR^{11}SO_2R^{13}$; —NCO; —$N_3$; —$NO_2$; —$S(O)_xR^{13}$; —$SO_2NR^{11}R^{12}$; —$C(R^{13})_zH_{(3-z)}$; —$(CH_2)_kR^{14}$; —$(CH_2)_k$—Z—$R^{16}$—; and —$(CH_2)_k$—Z—$(CH_2)_m$—$R^{14}$, where two or more R^e groups may optionally be taken together to form an optionally substituted ring; and $R^{10}$, $R^{11}$, $R^{12}$, $R^{13}$, $R^{14}$, $R^{16}$, Z, k, m, x, and z are as defined in claim 1.

49. The method of claim 36, wherein the statin molecule is simvastatin.

50. The method of claim 35, wherein the

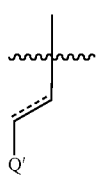

moiety is selected from the group consisting of:

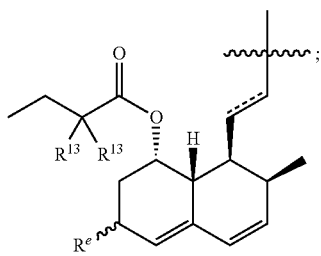

wherein R^e at each occurrence is independently selected from the group consisting of: hydrogen; $C_1$-$C_{12}$ alkyl; $C_2$-$C_{12}$ alkenyl; $C_2$-$C_{12}$ alkynyl; aryl; heteroaryl; halogen; —$OR^{10}$; —$OC(O)R^{13}$; —$OC(O)OR^{13}$; —$OC(O)NR^{11}R^{12}$; —CN; —CNO; —$C(O)R^{13}$; —$C(R^{13})_zH_{(3-z)}$; —$C(O)OR^{13}$; —$C(O)NR^{11}R^{12}$; —$NR^{11}R^{12}$; —$NR^{11}C(O)R^{10}$; —$NR^{11}C(O)OR^{13}$; —$NR^{11}SO_2R^{13}$; —NCO; —$N_3$; —$NO_2$; —$S(O)_xR^{13}$; —$SO_2NR^{11}R^{12}$; —$C(R^{13})_zH_{(3-z)}$; —$(CH_2)_kR^{14}$; —$(CH_2)_k$—Z—$R^{16}$—; and —$(CH_2)_k$—Z—$(CH_2)_m$—$R^{14}$, where two or more R^e groups may optionally be taken together to form an optionally substituted ring; and $R^{10}$, $R^{11}$, $R^{12}$, $R^{13}$, $R^{14}$, $R^{16}$, Z, k, m, x, and z are as defined in claim 1.

51. The method of claim 6, wherein X is a phosphorous-containing moiety selected from the group consisting of a phosphonium salt, a triarylphosphonium, and a phosphonate group.

52. The method of claim 51, wherein the phosphorous containing moiety is a phosphonium salt.

53. The method of claim 52, wherein the phosphonium salt has the formula —$[P(R^{13})_3]^+$.

54. The method of claim 53, wherein the phosphonium salt is a triarylphosphonium salt.

55. The method of claim 54, wherein the triarylphosphonium salt is triphenylphosphonium.

56. The method of claim 51, wherein the phosphorous containing moiety is a phosphonate.

57. The method of claim 56, wherein the phosphonate has the formula —P=$O(OR^{10})_2$.

58. The method of claim 56, wherein the phosphonate is a dialkyl phosphonate.

59. The method of claim 58, wherein the dialkyl phosphonate is selected from the group consisting of dimethyl phosphonate, diethyl phosphonate, di-n-propyl phosphonate, di-1-propyl phosphonate, and dibutyl phosphonate.

* * * * *